US011167014B2

(12) United States Patent
Vegge et al.

(10) Patent No.: US 11,167,014 B2
(45) Date of Patent: Nov. 9, 2021

(54) SOLID GLP-1 DERIVATIVE COMPOSITIONS FOR ORAL ADMINISTRATION

(71) Applicant: Novo Nordisk A/S, Bagsvaerd (DK)

(72) Inventors: Andreas Vegge, Frederiksberg (DK); Susanne Scheele, Staffanstorp (SE); Simon Bjerregaard, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/620,363

(22) PCT Filed: Jun. 11, 2018

(86) PCT No.: PCT/EP2018/065266
§ 371 (c)(1),
(2) Date: Dec. 6, 2019

(87) PCT Pub. No.: WO2018/224689
PCT Pub. Date: Dec. 13, 2018

(65) Prior Publication Data
US 2020/0147179 A1    May 14, 2020

(30) Foreign Application Priority Data
Jun. 9, 2017   (EP) .................................... 17175131

(51) Int. Cl.
*A61K 38/00* (2006.01)
*A61K 38/26* (2006.01)
*A61K 31/19* (2006.01)
*A61K 31/7034* (2006.01)

(52) U.S. Cl.
CPC .............. *A61K 38/26* (2013.01); *A61K 31/19* (2013.01); *A61K 31/7034* (2013.01)

(58) Field of Classification Search
CPC .... A61K 38/26; A61K 31/19; A61K 31/7048; A61P 3/10; A61P 3/08; A61P 3/04
See application file for complete search history.

(56) References Cited

U.S. PATENT DOCUMENTS

| | | |
|---|---|---|
| 6,515,117 B2 | 2/2003 | Ellsworth et al. |
| 6,936,590 B2 | 8/2005 | Washburn et al. |
| 7,919,598 B2 | 4/2011 | Gougoutas et al. |
| 8,871,264 B2 | 10/2014 | Hallgren et al. |
| 9,266,940 B2 | 2/2016 | Wieczorek et al. |
| 9,278,123 B2 | 3/2016 | Sauerberg et al. |
| 10,086,047 B2 | 10/2018 | Sauerberg et al. |
| 10,335,369 B2 | 7/2019 | Vilhelmsen |
| 2012/0071403 A1 | 3/2012 | Strumph et al. |
| 2013/0035281 A1* | 2/2013 | Klein ............... A61K 38/26 514/1.9 |
| 2014/0087996 A1 | 3/2014 | Klein et al. |
| 2015/0072926 A1 | 3/2015 | Vilhelmsen et al. |
| 2015/0150811 A1* | 6/2015 | Jensen ................. A61K 9/1617 424/465 |
| 2016/0296602 A1 | 10/2016 | Johansen |
| 2018/0360918 A1 | 12/2018 | Sauerberg et al. |
| 2019/0314283 A1 | 10/2019 | Vilhelmsen |
| 2019/0374614 A1 | 12/2019 | Skibsted et al. |

FOREIGN PATENT DOCUMENTS

| | | | |
|---|---|---|---|
| WO | 2006097537 | 9/2006 | |
| WO | 2008116179 A1 | 9/2008 | |
| WO | 2008144346 A2 | 11/2008 | |
| WO | 2011080103 A1 | 7/2011 | |
| WO | WO-2012080471 A * | 6/2012 | ................. A61P 3/10 |
| WO | 2012140117 A1 | 10/2012 | |
| WO | 2013032934 A1 | 3/2013 | |
| WO | 2015155151 A1 | 10/2015 | |
| WO | 2017004623 A1 | 1/2017 | |
| WO | WO-2017004623 A1 * | 1/2017 | ........... A61K 9/4825 |
| WO | 18096163 A1 | 5/2018 | |
| WO | 18096164 A1 | 5/2018 | |

OTHER PUBLICATIONS

Martinez et al. Real-world effectiveness and safety of dapagliflozin therapy added to a GLP1 receptor agonist in patients with type 2 diabetes. 2017. Nutrition, Metabolism & Cardiovascular Diseases (2017) 27, 129-137 (Year: 2017).*
Border et al., "Addition of GLP-1 Agonist ('Bydureon') and SGLT-2 Inhibitor (Dapagliflozin) Combination Therapy: A Case of Significant Weight Loss and Improved Glycaemic Control in a Poorly-Controlled Patient with Concurrent Depression," Diabetic Medicine, 2017, vol. 34, Suppl. S1, pp. 36-194.
Deol et al., "Combination therapy with GLP-1 analogues and SGLT-2 inhibitors in the management of diabesity: the real world experience" Endocrine, 2016, vol. 55, No. 1, pp. 173-178.
Engeli et al., "Blood Pressure Effects of Glucagon-Like Peptide 1 Analogues and Sodium Glucose Transporter 2 Inhibitors," Pharmacology and Therapeutics, 2014, vol. 23, No. 5, pp. 468-472.
Frias et al., "Exenatide Once Weekly Plus Dapagliflozin Once Daily Versus Exenatide or Dapagliflozin Alone in Patients with Type 2 Diabetes Inadequately Controlled with Metformin Monotherapy (DURATION-8): a 28 Week, Multicentre, Double-Blind, Phase 3, Radomized Controlled Trial," The Lancet/Diabetes & Endocrinology, 2016, vol. 4, No. 12, pp. 1004-1016.
Gorgojo-Martinez et al., "Real-World Effectiveness and Safety of Dapagliflozin Therapy Added to a GLP1 Receptor Agonist in Patients with Type 2 Diabetes," Nutrition, Metabolism & Cardiovascular Diseases, 2017, vol. 27, pp. 129-137.
Kohei Kaku et al., "Dapagliflozin as Monotherapy or Combination Therapy in Japanese Patients with Type 2 Diabetes: An Open-Label Study," Diabetes Therapy, 2014, vol. 5, pp. 415-433.

(Continued)

*Primary Examiner* — James H Alstrum-Acevedo
*Assistant Examiner* — Mercy H Sabila
(74) *Attorney, Agent, or Firm* — Rosemarie R. Wilk-Orescan

(57) ABSTRACT

The present invention relates to solid compositions for oral administration comprising (i) a GLP-1 derivative and the SGLT2 inhibitor dapagliflozin or (ii) a GLP-1 derivative and a salt of NAC in combination with an SGLT2 inhibitor.

15 Claims, No Drawings

Specification includes a Sequence Listing.

(56) References Cited

OTHER PUBLICATIONS

Rizzo et al., "Dapagliflozin Therapy in Type-2 Diabetes: Current Knowledge and Future Perspectives," Expert Opinion n Pharmacotherapy, 2015, vol. 16, No. 3, pp. 281-284.

Steinert et al., Am I Clin Nutr, Oct. 2010, vol. 92, pp. 810-817.

Tatarkiewicz et al., "Combined Antidiabetic Benefits of Exenatide and Dapagliflozin in Diabetic Mice," Diabetes, Obesity and Metabolism, 2014, vol. 16, pp. 376-380.

Zou et al., "SGLT2 Inhibitors: A Novel Choice for the Combination Therapy in Diabetic Kidney Disease," Cardiovascular Diabetology, 2017, vol. 16, pp. 65-76.

* cited by examiner

SEQUENCE LISTING

<160> NUMBER OF SEQ ID NOS: 8

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 33
<212> TYPE: PRT
<213> ORGANISM: ARTIFICIAL
<220> FEATURE:
<223> OTHER INFORMATION: Based on human GLP-1
<220> FEATURE:
<221> NAME/KEY: SITE
<222> LOCATION: (1)..(1)
<223> OTHER INFORMATION: This residue is L-His, imidazopropionyl,
      alpha-hydroxy-histidine, D-His, desamino-His, 2-amino-His,
      beta-hydroxy-His, homo-His, N-alpha-acetyl-His,
      N-alpha-formyl-His, alpha-fluoromethyl-His, alpha-methyl-His,
      3-pyridyl-Ala, 2-pyridyl-Ala, or 4-pyridyl-Ala
<220> FEATURE:
<221> NAME/KEY: SITE
<222> LOCATION: (2)..(2)
<223> OTHER INFORMATION: This residue is Ala, Gly, Val, Leu, Ile, Thr,
      Ser, Lys, Aib, (1-aminocyclopropyl) carboxylic acid,
      (1-aminocyclobutyl) carboxylic acid (CA), (1-aminocyclopentyl) CA,
      (1-aminocyclohexyl) CA, (1-aminocycloheptyl) CA, or
<220> FEATURE:
<221> NAME/KEY: SITE
<222> LOCATION: (6)..(6)
<223> OTHER INFORMATION: This residue is Lys or Phe
<220> FEATURE:
<221> NAME/KEY: SITE
<222> LOCATION: (10)..(10)
<223> OTHER INFORMATION: This residue is Val or Leu
<220> FEATURE:
<221> NAME/KEY: SITE
<222> LOCATION: (12)..(12)
<223> OTHER INFORMATION: This residue is Ser, Arg, Asn, Gln, or Glu
<220> FEATURE:
<221> NAME/KEY: SITE
<222> LOCATION: (13)..(13)
<223> OTHER INFORMATION: This residue is Tyr or Gln
<220> FEATURE:
<221> NAME/KEY: SITE
<222> LOCATION: (14)..(14)
<223> OTHER INFORMATION: This residue is Leu, Lys, or Met
<220> FEATURE:
<221> NAME/KEY: SITE
<222> LOCATION: (16)..(16)
<223> OTHER INFORMATION: This residue is Gly, Glu, Lys, or Aib
<220> FEATURE:
<221> NAME/KEY: SITE
<222> LOCATION: (17)..(17)
<223> OTHER INFORMATION: This residue is Gln, Glu, or Arg
<220> FEATURE:
<221> NAME/KEY: SITE
<222> LOCATION: (18)..(18)
<223> OTHER INFORMATION: This residue is Ala or Lys
<220> FEATURE:
<221> NAME/KEY: SITE
<222> LOCATION: (19)..(19)
<223> OTHER INFORMATION: This residue is Ala or Val
<220> FEATURE:
<221> NAME/KEY: SITE
<222> LOCATION: (20)..(20)
<223> OTHER INFORMATION: This residue is Val, His, Lys or Arg
<220> FEATURE:

```
<221> NAME/KEY: SITE
<222> LOCATION: (24)..(24)
<223> OTHER INFORMATION: This residue is Ala, Glu, or Arg
<220> FEATURE:
<221> NAME/KEY: SITE
<222> LOCATION: (25)..(25)
<223> OTHER INFORMATION: This residue is Trp or His
<220> FEATURE:
<221> NAME/KEY: SITE
<222> LOCATION: (28)..(28)
<223> OTHER INFORMATION: This residue is Glu, Asn, Gly, Gln, or Arg
<220> FEATURE:
<221> NAME/KEY: SITE
<222> LOCATION: (29)..(29)
<223> OTHER INFORMATION: This residue is Gly, Aib, or absent
<220> FEATURE:
<221> NAME/KEY: SITE
<222> LOCATION: (30)..(30)
<223> OTHER INFORMATION: This residue is Arg, Gly, Lys, or absent
<220> FEATURE:
<221> NAME/KEY: SITE
<222> LOCATION: (31)..(31)
<223> OTHER INFORMATION: This residue is Gly, Ala, Glu, Pro, Lys, Arg,
      or absent
<220> FEATURE:
<221> NAME/KEY: SITE
<222> LOCATION: (32)..(32)
<223> OTHER INFORMATION: This residue is Ser, Gly, Ala, Glu, Gln, Pro,
      Arg, or absent
<220> FEATURE:
<221> NAME/KEY: SITE
<222> LOCATION: (33)..(33)
<223> OTHER INFORMATION: This residue is Gly or absent

<400> SEQUENCE: 2

Xaa Xaa Glu Gly Thr Xaa Thr Ser Asp Xaa Ser Xaa Xaa Xaa Glu Xaa
1               5                   10                  15

Xaa Xaa Xaa Xaa Lys Phe Ile Xaa Xaa Leu Val Xaa Xaa Xaa Xaa Xaa
            20                  25                  30

Xaa

<210> SEQ ID NO 3
<211> LENGTH: 31
<212> TYPE: PRT
<213> ORGANISM: ARTIFICIAL
<220> FEATURE:
<223> OTHER INFORMATION: Based on human GLP-1
<220> FEATURE:
<221> NAME/KEY: SITE
<222> LOCATION: (2)..(2)
<223> OTHER INFORMATION: This amino acid residue is Aib
<220> FEATURE:
<221> NAME/KEY: SITE
<222> LOCATION: (20)..(20)
<223> OTHER INFORMATION: This amino acid residue is covalently attached
      to a substituent
<220> FEATURE:
<221> NAME/KEY: SITE
<222> LOCATION: (31)..(31)
<223> OTHER INFORMATION: This amino acid residue is covalently attached
      to a substituent

<400> SEQUENCE: 3

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Lys
            20                  25                  30

<210> SEQ ID NO 4
<211> LENGTH: 33
<212> TYPE: PRT
<213> ORGANISM: ARTIFICIAL
```

```
<220> FEATURE:
<223> OTHER INFORMATION: Based on human GLP-1
<220> FEATURE:
<221> NAME/KEY: SITE
<222> LOCATION: (2)..(2)
<223> OTHER INFORMATION: This amino acid residue is Aib
<220> FEATURE:
<221> NAME/KEY: SITE
<222> LOCATION: (21)..(21)
<223> OTHER INFORMATION: This amino acid residue is covalently attached
      to a substituent
<220> FEATURE:
<221> NAME/KEY: SITE
<222> LOCATION: (30)..(30)
<223> OTHER INFORMATION: This amino acid residue is covalently attached
      to a substituent

<400> SEQUENCE: 4

His Xaa Glu Gly Thr Phe Thr Ser Asp Val Ser Ser Tyr Leu Glu Glu
1               5                   10                  15

Gln Ala Ala Arg Lys Phe Ile Gly Trp Leu Val Arg Gly Lys Gly Glu
            20                  25                  30

Gly

<210> SEQ ID NO 5
<211> LENGTH: 31
<212> TYPE: PRT
<213> ORGANISM: ARTIFICIAL
<220> FEATURE:
<223> OTHER INFORMATION: Based on human GLP-1
<220> FEATURE:
<221> NAME/KEY: SITE
<222> LOCATION: (1)..(1)
<223> OTHER INFORMATION: This residue (Xaa7) is L-His,
      (S)-2-Hydroxy-3-(1H-imidazol-4-yl)-propionic acid, D-His,
      desamino-His, Nalpha-acetyl-His, or Nalpha-formyl-His
<220> FEATURE:
<221> NAME/KEY: SITE
<222> LOCATION: (2)..(2)
<223> OTHER INFORMATION: This residue (Xaa8) is Ala, Ser, Aib,
      (1-aminocyclopropyl) carboxylic acid, or (1-aminocyclobutyl)
      carboxylic acid
<220> FEATURE:
<221> NAME/KEY: SITE
<222> LOCATION: (10)..(10)
<223> OTHER INFORMATION: This residue (Xaa16) is Val or Leu
<220> FEATURE:
<221> NAME/KEY: SITE
<222> LOCATION: (12)..(12)
<223> OTHER INFORMATION: This residue (Xaa18) is Ser or Arg
<220> FEATURE:
<221> NAME/KEY: SITE
<222> LOCATION: (13)..(13)
<223> OTHER INFORMATION: This residue (Xaa19) is Tyr or Gln
<220> FEATURE:
<221> NAME/KEY: SITE
<222> LOCATION: (14)..(14)
<223> OTHER INFORMATION: This residue (Xaa20) is Leu or Met
<220> FEATURE:
<221> NAME/KEY: SITE
<222> LOCATION: (16)..(16)
<223> OTHER INFORMATION: This residue (Xaa22) is Gly or Glu
<220> FEATURE:
<221> NAME/KEY: SITE
<222> LOCATION: (17)..(17)
<223> OTHER INFORMATION: This residue (Xaa23) is Gln, Glu, or Arg
<220> FEATURE:
<221> NAME/KEY: SITE
<222> LOCATION: (19)..(19)
<223> OTHER INFORMATION: This residue (Xaa25) is Ala or Val
<220> FEATURE:
<221> NAME/KEY: SITE
<222> LOCATION: (20)..(20)
<223> OTHER INFORMATION: This residue (Xaa26) is Arg or Lys
<220> FEATURE:
```

```
<221> NAME/KEY: SITE
<222> LOCATION: (21)..(21)
<223> OTHER INFORMATION: This residue (Xaa27) is Glu or Leu
<220> FEATURE:
<221> NAME/KEY: SITE
<222> LOCATION: (24)..(24)
<223> OTHER INFORMATION: This residue (Xaa30) is Ala or Glu
<220> FEATURE:
<221> NAME/KEY: SITE
<222> LOCATION: (25)..(25)
<223> OTHER INFORMATION: This residue (Xaa31) is Trp or His
<220> FEATURE:
<221> NAME/KEY: SITE
<222> LOCATION: (27)..(27)
<223> OTHER INFORMATION: This residue (Xaa33) is Val or Arg
<220> FEATURE:
<221> NAME/KEY: SITE
<222> LOCATION: (28)..(28)
<223> OTHER INFORMATION: This residue (Xaa34) is Arg, Lys, His, Asn,
     or Gln
<220> FEATURE:
<221> NAME/KEY: SITE
<222> LOCATION: (29)..(29)
<223> OTHER INFORMATION: This residue (Xaa35) is Gly or Aib

<400> SEQUENCE: 5

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Lys Lys
            20                  25                  30

<210> SEQ ID NO 6
<211> LENGTH: 31
<212> TYPE: PRT
<213> ORGANISM: ARTIFICIAL
<220> FEATURE:
<223> OTHER INFORMATION: Based on human GLP-1
<220> FEATURE:
<221> NAME/KEY: SITE
<222> LOCATION: (2)..(2)
<223> OTHER INFORMATION: This amino acid residue is Aib
<220> FEATURE:
<221> NAME/KEY: SITE
<222> LOCATION: (30)..(30)
<223> OTHER INFORMATION: This amino acid residue is covalently attached
     to a substituent
<220> FEATURE:
<221> NAME/KEY: SITE
<222> LOCATION: (31)..(31)
<223> OTHER INFORMATION: This amino acid residue is covalently attached
     to a substituent

<400> SEQUENCE: 6

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Lys
            20                  25                  30

<210> SEQ ID NO 7
<211> LENGTH: 31
<212> TYPE: PRT
<213> ORGANISM: ARTIFICIAL
<220> FEATURE:
<223> OTHER INFORMATION: Based on human GLP-1
<220> FEATURE:
<221> NAME/KEY: SITE
<222> LOCATION: (2)..(2)
<223> OTHER INFORMATION: This amino acid residue is Aib
<220> FEATURE:
<221> NAME/KEY: SITE
<222> LOCATION: (30)..(30)
<223> OTHER INFORMATION: This amino acid residue is covalently attached
     to a substituent
```

```
<220> FEATURE:
<221> NAME/KEY: SITE
<222> LOCATION: (31)..(31)
<223> OTHER INFORMATION: This amino acid residue is covalently attached
      to a substituent

<400> SEQUENCE: 7

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Lys
            20                  25                  30

<210> SEQ ID NO 8
<211> LENGTH: 31
<212> TYPE: PRT
<213> ORGANISM: ARTIFICIAL
<220> FEATURE:
<223> OTHER INFORMATION: GLP-1 agonist based on from human GLP-1
<220> FEATURE:
<221> NAME/KEY: SITE
<222> LOCATION: (2)..(2)
<223> OTHER INFORMATION: Aib
<220> FEATURE:
<221> NAME/KEY: SITE
<222> LOCATION: (30)..(30)
<223> OTHER INFORMATION: This amino acid residue is covalently attached
      to a substituent
<220> FEATURE:
<221> NAME/KEY: SITE
<222> LOCATION: (31)..(31)
<223> OTHER INFORMATION: This amino acid residue is covalently attached
      to a substituent

<400> SEQUENCE: 8

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Lys
            20                  25                  30
```

SOLID GLP-1 DERIVATIVE COMPOSITIONS FOR ORAL ADMINISTRATION

CROSS-REFERENCE TO RELATED APPLICATIONS

This application is a 35 U.S.C. § 371 National Stage application of International Application PCT/EP2018/065266 (WO/2018/224689), filed Jun. 11, 2018, which claims priority to European Patent Application 17175131.6, filed Jun. 9, 2017, the contents of all above-named applications are incorporated herein by reference.

The present invention relates to solid compositions for oral administration.

BACKGROUND

GLP-1 peptides have a low oral bioavailability. GLP-1 peptides can only be detected in plasma after oral administration if formulated with certain absorption enhancers. There is a need for a further improved pharmaceutical composition for oral administration of GLP-1 peptides.

SUMMARY

In some embodiments the present invention relates to a solid composition for oral administration comprising (i) a GLP-1 derivative and dapagliflozin, or (ii) a GLP-1 derivative and a salt of NAC in combination with a sodium glucose linked transporter 2 (SGLT2) inhibitor.

DESCRIPTION

The present inventors surprisingly found that compositions comprising dapagliflozin in combination with a GLP-1 derivative or SNAC provide improved permeability of said GLP-1 derivative through a cellular membrane. In some embodiments the composition of the invention provides improved bioavailability of a GLP-1 peptide or a derivative thereof. In some embodiments the present invention relates to a solid composition for oral administration comprising a GLP-1 derivative and dapagliflozin. Further, the present inventors surprisingly found that compositions comprising dapagliflozin in combination with a GLP-1 derivative or SNAC provide improved permeability through a cellular membrane of dapagliflozin and/or a GLP-1 peptide or a derivative thereof. In some embodiments the composition of the invention provides improved bioavailability of dapagliflozin and/or a GLP-1 peptide or a derivative thereof.

The present inventors also surprisingly found that compositions comprising empagliflozin in combination with a GLP-1 derivative and SNAC provide improved permeability of said GLP-1 derivative through a cellular membrane. In some embodiments the present invention relates to a solid composition for oral administration comprising a GLP-1 derivative and a salt of NAC in combination with an SGLT2 inhibitor. In some embodiments the present invention relates to a solid composition for oral administration comprising a GLP-1 derivative, a salt of NAC (e.g. SNAC), and empagliflozin.

In some embodiments the invention relates to a solid composition comprising a GLP-1 derivative and dapagliflozin. In some embodiments said composition is for oral administration. In some embodiments said GLP-1 derivative is selected from the group consisting of semaglutide, Compound A, Compound B, Compound C, Compound D, and Compound E. In some embodiments said composition further comprises an absorption enhancer. In some embodiments said absorption enhancer is a salt of NAC, such as SNAC. In some embodiments the invention relates to a solid composition comprising dapagliflozin and SNAC, wherein said composition optionally further comprises a GLP-1 peptide or a derivative thereof. In some embodiments the invention relates to a solid composition for oral administration comprising a GLP-1 derivative and second active ingredient, wherein said second active ingredient inhibits glucose reuptake via the SGLT2 receptor and increases permeability of said GLP-1 derivative through a cellular mono layer.

A solid composition for oral administration comprising a GLP-1 derivative and dapagliflozin further provides patient convenience.

In some embodiments the composition is administered once daily. In some embodiments the composition is administered in a dosage in the range of 100-1500 mg, such as 200-1000 mg. In some embodiments the weight of the tablet is in the range of 150 mg to 1000 mg, such as in the range of 300-600 mg or such as 300-500 mg.

In some embodiments the composition comprises the GLP-1 peptide or the GLP-1 derivative in an amount of 0.1-100 mg, such as 0.2-60 mg. In some embodiments the composition comprises the GLP-1 peptide or the GLP-1 derivative in an amount of 1-30 mg, such as 2-20 mg. In some embodiments the composition comprises 0.5-300 mg, such as 5-100 mg, SGLT2 inhibitor. In some embodiments the composition comprises 3-50 mg, such as 5-30 mg, SGLT2 inhibitor. In some embodiments the composition comprises 5-300 mg SGLT2 inhibitor, 0.1-100 mg GLP-1 derivative, and 20-800 mg salt of NAC, such as SNAC. In some embodiments the composition comprises 0.5-50 mg dapagliflozin, such as 2-15 mg dapagliflozin. In some embodiments the composition comprises 5 or 10 mg dapagliflozin. In some embodiments the composition comprises 0.5-50 mg dapagliflozin and 0.1-100 mg GLP-1 derivative. In some embodiments the composition comprises 0.5 to 50 mg empagliflozin. In some embodiments the composition comprises 5-30 mg empagliflozin, such as 10 or 25 mg empagliflozin. In some embodiments the composition comprises 20-800 mg salt of NAC, such as SNAC. In some embodiments the composition comprises 20-1000 mg, such as 50-800 mg or 100-600 mg, salt of NAC. In some embodiments the composition comprises 100-500 mg, such as 200-400 mg or 300 mg, salt of NAC. In some embodiments the composition comprises 0.5-300 mg SGLT2 inhibitor, 0.1-100 mg GLP-1 derivative, and 20-800 mg salt of NAC, such as SNAG. In some embodiments the ratio between the SGLT2 inhibitor and the GLP-1 derivative is from 0.1 to 100 based on weight.

In some embodiments the dosage of said GLP-1 peptide or said GLP-1 derivative is from 0.1 to 100 mg per day, such as from 0.1 to 60 mg per day. In some embodiments the dosage of dapagliflozin is from 0.5 to 50 mg per day. In some embodiments the dosage of said dapagliflozin is 0.5-50 mg per day and the dosage of said GLP-1 derivative is 0.1-100 mg per day. In some embodiments the dosage of said salt of NAC, such as SNAG, is from 20 to 800 mg per day. In some embodiments the dosage of empagliflozin is from 0.5 to 50 mg per day.

GLP-1 Peptides

In some embodiments the composition of the present invention comprises a GLP-1 peptide. The term "GLP-1 peptide" refers to a peptide which a variant of human GLP-1 with GLP-1 activity. The term "human GLP-1" as used herein means the human GLP-1 hormone whose structure and properties are well-known. Human GLP-1 is also denoted GLP-1(7-37), it has 31 amino acids and results from selective cleavage of the proglucagon molecule. The amino acid sequence of human GLP-1 is HAEGTFTSDV SSYLEGQAAKEFIAWLVKGRG (SEQ ID NO: 1).

In some embodiments the GLP-1 peptide comprises no more than 10 substitutions, deletions and/or additions of amino acids relative to human GLP-1 or exendin-4. In particular, the GLP-1 peptide comprises no more than 8, such as no more than 6, no more than 5, or no more than 4, substitutions, deletions and/or additions of amino acids relative to human GLP-1. The GLP-1 peptide may comprise no more than 8 substitutions, deletions and/or additions of amino acids relative to human GLP-1.

The GLP-1 peptides of the invention are GLP-1 receptor agonists (this may also be referred to as "GLP-1 activity"). A receptor agonist may be defined as a compound that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763). Thus, for example, a "GLP-1 receptor agonist" (also referred to herein as a "GLP-1 agonist") may be defined as a compound which is capable of binding to the GLP-1 receptor and capable of activating it. And a "full" GLP-1 receptor agonist may be defined as a GLP-1 receptor agonist which is capable of eliciting a magnitude of GLP-1 receptor response that is similar to human GLP-1. In some embodiments the GLP-1 agonist is a full GLP-1 receptor agonist. For example, the GLP-1 peptides of the invention can be tested for GLP-1 activity using a standard GLP-1 activity assay.

In the sequence listing, the first amino acid residue of SEQ ID NO: 1 (histidine) is assigned no. 1. However, in what follows—according to established practice in the art—this histidine residue is referred to as no. 7, and subsequent amino acid residues are numbered accordingly, ending with glycine no. 37. Therefore, generally, any reference herein to an amino acid residue number or a position number of the GLP-1(7-37) sequence is to the sequence starting with His at position 7 and ending with Gly at position 37.

GLP-1 peptides of the invention may be described by reference to i) the number of the amino acid residue in human GLP-1(7-37) which corresponds to the amino acid residue which is changed (i.e., the corresponding position in human GLP-1), and to ii) the actual change.

In other words, a GLP-1 peptide is human GLP-1(7-37) in which a number of amino acid residues have been changed when compared to human GLP-1(7-37) (SEQ ID NO: 1). These changes may represent, independently, one or more amino acid substitutions, additions, and/or deletions.

The following are non-limiting examples of suitable nomenclature.

GLP-1 peptides "comprising" certain specified changes may comprise further changes, when compared to SEQ ID NO: 1. In some embodiments the GLP-1 peptide "has" the specified changes.

As is apparent from the above examples, amino acid residues may be identified by their full name, their one-letter code, and/or their three-letter code. These three ways are fully equivalent.

The expressions "a position corresponding to" or "corresponding position" may be used to characterise the site of change in a variant GLP-1(7-37) sequence by reference to human GLP-1(7-37) (SEQ ID NO: 1). Equivalent or corresponding positions, as well as the number of changes, are easily deduced, e.g. by simple handwriting and eyeballing; and/or a standard protein or peptide alignment program may be used, such as "align" which is based on a Needleman-Wunsch algorithm. This algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

In case of non-natural amino acids such as Imp and/or Aib being included in the sequence, these may, for alignment purposes, be replaced with, e.g., X. If desired, X can later be manually corrected.

The term "peptide", as e.g. used in the context of the GLP-1 peptides of the invention, refers to a compound which comprises a series of amino acids interconnected by amide (or peptide) bonds. The peptides of the invention comprise at least five constituent amino acids connected by peptide bonds. In particular embodiments the peptide comprises at least 10, preferably at least 15, more preferably at least 20, even more preferably at least 25, or most preferably at least 28 amino acids. In particular embodiments, the peptide is composed of at least five constituent amino acids, preferably composed of at least 10, at least 15, at least 20, at least 25, or most preferably composed of at least 28 amino acids. In additional particular embodiments, the peptide a) is composed of, or b) consists of 29-33 amino acids. In some embodiments the peptide consists of 29, 30, or 31 amino acids. In some embodiments the peptide consists of 32, 33 or 34 amino acids. In a still further particular embodiment the peptide consists of amino acids interconnected by peptide bonds.

Amino acids are molecules containing an amine group and a carboxylic acid group, and, optionally, one or more additional groups, often referred to as a side chain.

The term "amino acid" includes proteinogenic (or natural) amino acids (amongst those the 20 standard amino acids), as well as non-proteinogenic (or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification). Non-limiting examples of non-proteinogenic amino acids are Aib (α-aminoisobutyric acid), des-amino-histidine (alternative name imidazopropionic acid, abbreviated Imp), as well as the D-isomers of the proteinogenic amino acids. In what follows, all amino acids of the GLP-1 peptide for which the optical isomer is not stated is to be understood to mean the L-isomer (unless otherwise specified).

In some embodiments the GLP-1 peptide comprises Formula I:

Formula I: Xaa7-Xaa8-Glu-Gly-Thr-Xaa12-Thr-Ser-Asp-Xaa16-Ser-Xaa18-Xaa19-Xaa20-Glu-Xaa22-Xaa23-Xaa24-Xaa25-Xaa26-Lys-Phe-Ile-Xaa30-Xaa31-Leu-Val-Xaa34-Xaa35-Xaa36-Xaa37-Xaa38-Xaa39 (SEQ ID NO: 2), wherein Xaa7 is L-histidine, imidazopropionyl, α-hydroxy-histidine, D-histidine, desamino-histidine, 2-amino-histidine, β-hydroxy-histidine, homohistidine, Nα-acetyl-histidine, Nα-formyl-histidine, α-fluoromethyl-histidine, α-methyl-histidine, 3-pyridylalanine, 2-pyridylalanine, or 4-pyridylalanine;

Xaa8 is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

Xaa12 is Lys or Phe;
Xaa16 is Val or Leu;
Xaa18 is Ser, Arg, Asn, Gln, or Glu;
Xaa19 is Tyr or Gln;
Xaa20 is Leu, Lys, or Met;
Xaa22 is Gly, Glu, Lys, or Aib;
Xaa23 is Gln, Glu, or Arg;
Xaa24 is Ala or Lys;
Xaa25 is Ala or Val;
Xaa26 is Val, His, Lys or Arg;
Xaa30 is Ala, Glu, or Arg;
Xaa31 is Trp or His;
Xaa34 is Glu, Asn, Gly, Gln, or Arg;
Xaa35 is Gly, Aib, or absent;
Xaa36 is Arg, Gly, Lys, or absent;
Xaa37 is Gly, Ala, Glu, Pro, Lys, Arg, or absent;
Xaa38 is Ser, Gly, Ala, Glu, Gln, Pro, Arg, or absent; and
Xaa39 is Gly or absent.

In some embodiments the GLP-1 peptide comprises or consists of Formula I. If Xaa38 of Formula I is absent, then Xaa39 of Formula I may also be absent. If Xaa37 of Formula I is absent, then Xaa38 and Xaa39 of Formula I may also be absent. If Xaa36 of Formula I is absent, then Xaa37, Xaa38, and Xaa39 of Formula I may also be absent. If Xaa35 of Formula I is absent, then Xaa36, Xaa37, Xaa38, and Xaa39 of Formula I may also be absent.

In some embodiments the GLP-1 peptide comprises Formula I, wherein Xaa7 is His; Xaa8 is Ala or Aib; Xaa12 is Lys or Phe; Xaa16 is Val; Xaa18 is Ser; Xaa19 is Tyr; Xaa20 is Leu or Lys; Xaa22 is Glu, Gly or Lys; Xaa23 is Glu or Gln; Xaa24 is Ala or Lys; Xaa25 is Ala or Val; Xaa26 is Lys or Arg; Xaa30 is Ala or Glu; Xaa31 is Trp or His; Xaa34 is Gly, Gln, or Arg; Xaa35 is Gly or absent; Xaa36 is Arg, Lys, or absent; Xaa37 is Gly, Lys, or absent; Xaa38 is Glu, Gln or absent; and Xaa39 is Gly or absent.

In some embodiments the GLP-1 peptide comprises Formula I, wherein Xaa7 is His; Xaa8 is Aib; Xaa12 is Phe; Xaa16 is Val; Xaa18 is Ser; Xaa19 is Tyr; Xaa20 is Leu; Xaa22 is Glu or Gly; Xaa23 is Gln; Xaa24 is Ala; Xaa25 is Ala; Xaa26 is Lys or Arg; Xaa30 is Ala or Glu; Xaa31 is Trp; Xaa34 is Arg; Xaa35 is Gly; Xaa36 is Arg or Lys; Xaa37 is Gly or Lys; Xaa38 is Glu or absent; and Xaa39 is Gly or absent.

GLP-1 Derivatives

In some embodiments the GLP-1 peptide is a derivative of a GLP-1 peptide (also referred to herein as a "GLP-1 derivative"). The term "derivative" as used herein in the context of a GLP-1 peptide means a chemically modified GLP-1 peptide, in which one or more substituents have been covalently attached to the constituent peptide. The substituent may also be referred to as a side chain. Thus, the term "derivative" as used herein in the context of a GLP-1 peptide means a chemically modified GLP-1 peptide, in which one or more substituents have been covalently attached to the peptide. The GLP-1 derivative may comprise a GLP-1 peptide covalently attached by acylation to a substituent, wherein said substituent comprises a lipophilic moiety and optionally a distal acidic (e.g. carboxylic acid) or aromatic group (e.g. 4-carboxyphenoxy).

In some embodiments said GLP-1 peptide or said GLP-1 derivative has a size of no more than 12 kDa, such as no more than 10 kDa, no more than 7 kDa, or no more than 4 kDa. In some embodiments said GLP-1 peptide or said GLP-1 derivative has a size (i.e. molecular weight) of 2-12 kDa, such as 3-6 kDa In some embodiments the side chain is capable of forming non-covalent aggregates with albumin, thereby promoting the circulation of the derivative with the blood stream, and also having the effect of protracting the time of action of the derivative, due to the fact that the aggregate of the GLP-1 derivative and albumin is only slowly disintegrated to release the drug substance. Thus, the substituent, or side chain, as a whole is preferably referred to as an albumin binding moiety.

In particular embodiments, the side chain has at least 10 carbon atoms, or at least 15, 20, 25, 30, 35, or at least 40 carbon atoms. In further particular embodiments, the side chain may further include at least 5 hetero atoms, in particular O and N, for example at least 7, 9, 10, 12, 15, 17, or at least 20 hetero atoms, such as at least 1, 2, or 3 N-atoms, and/or at least 3, 6, 9, 12, or 15 O-atoms.

In another particular embodiment the albumin binding moiety comprises a portion which is particularly relevant for the albumin binding and thereby the protraction, which portion may accordingly be referred to as a protracting moiety. The protracting moiety may be near, preferably at, the terminal (or distal, or free) end of the albumin binding moiety, relative to its point of attachment to the peptide.

In a still further particular embodiment the albumin binding moiety comprises a portion between the protracting moiety and the point of attachment to the peptide, which portion may be referred to as a linker, linker moiety, spacer, or the like. The linker may be optional, and hence in that case the albumin binding moiety may be identical to the protracting moiety.

In particular embodiments, the albumin binding moiety and/or the protracting moiety is lipophilic, and/or negatively charged at physiological pH (7.4).

The albumin binding moiety, the protracting moiety, or the linker may be covalently attached to a lysine residue of the constituent peptide (e.g. GLP-1 peptide) by acylation, i.e., via an amide bond formed between a carboxylic acid group thereof (of the albumin binding moiety, the protracting moiety, or the linker) and an amino group of the lysine residue. Additional or alternative conjugation chemistry includes alkylation, ester formation, or amide formation, or coupling to a cysteine residue, such as by maleimide or haloacetamide (such as bromo-/fluoro-/iodo-) coupling.

In some embodiments an active ester of the albumin binding moiety, preferably comprising a protracting moiety and a linker, is covalently linked to an amino group of a lysine residue, preferably the epsilon amino group thereof, under formation of an amide bond, as explained above.

Unless otherwise stated, when reference is made to an acylation of a lysine residue, it is understood to be to the epsilon-amino group thereof.

The term "fatty acid" refers to aliphatic monocarboxylic acids having from 4 to 28 carbon atoms, it is preferably un-branched, and it may be saturated or unsaturated.

The term "fatty diacid" refers to fatty acids as defined above but with an additional carboxylic acid group in the omega position. Thus, fatty diacids are dicarboxylic acids. The fatty diacid may comprise 14-22 carbon atoms.

Each of the two linkers of the derivative of the invention may comprise the following first linker element:

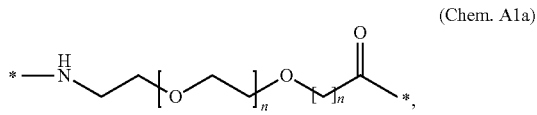

(Chem. A1a)

wherein k is an integer in the range of 1-5, and n is an integer in the range of 1-5.

In some embodiments, when k=1 and n=1, this linker element may be designated OEG, or a di-radical of 8-amino-3,6-dioxaoctanic acid, and/or it may be represented by the following formula:

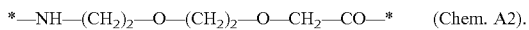

(Chem. A2).

In some embodiments each linker of the derivative of the invention may further comprise, independently, a second linker element, preferably a Glu di-radical, such as Chem. B1:

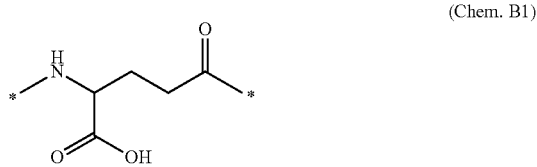

(Chem. B1)

wherein the Glu di-radical may be included p times, where p is an integer in the range of 1-3. Chem. B1 may also be referred to as gamma-Glu, or briefly gGlu, due to the fact that it is the gamma carboxy group of the amino acid glutamic acid which is here used for connection to another linker element, or to the epsilon-amino group of lysine. As explained above, the other linker element may, for example, be another Glu residue, or an OEG molecule. The amino group of Glu in turn forms an amide bond with the carboxy group of the protracting moiety, or with the carboxy group of, e.g., an OEG molecule, if present, or with the gamma-carboxy group of, e.g., another Glu, if present.

As explained above, the GLP-1 derivatives may be double-acylated, i.e. two albumin binding moieties are covalently attached to the constituent peptide (e.g. GLP-1 peptide).

In some embodiments the two albumin binding moieties (i.e. the entire side chains) are similar, preferably substantially identical, or, most preferably, identical.

In some embodiments the two protracting moieties are similar, preferably substantially identical, or, most preferably, identical.

In some embodiments the two linkers are similar, preferably substantially identical, or, most preferably identical.

The term "substantially identical" includes differences from identity which are due to formation of one or more salts, esters, and/or amides; preferably formation of one or more salts, methyl esters, and simple amides; more preferably formation of no more than two salts, methyl esters, and/or simple amides; even more preferably formation of no more than one salt, methyl ester, and/or simple amide; or most preferably formation of no more than one salt.

In the context of chemical compounds such as the albumin binding moieties, protracting moieties, and linkers, similarity and/or identity may be determined using any suitable computer program and/or algorithm known in the art.

For example, the similarity of two protracting moieties, two linkers, and/or two entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protracting moieties, the two linkers, and/or the two entire side chains are represented as a) ECFP_6 fingerprints; b) UNITY fingerprints; and/or c) MDL fingerprints. The Tanimoto coefficient is preferably used for calculating the similarity of the two fingerprints, whether a), b), or c) is used. In particular embodiments, whether a), b), or c) is used, the two protracting moieties, the two linkers, and/or the two entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008—both from Accelrys Software Inc., San Diego, US, and the guides http://www.tripos.com/tripos_resources/fileroot/pdfs/Unity_111408.pdf, and http://www.tripos.com/data/SYBYL/SYBYL_072505.pdf.

An example of a similarity calculation is inserted hereinbelow, in which a known entire side chain of a known GLP-1 derivative was compared with a methyl ester thereof:

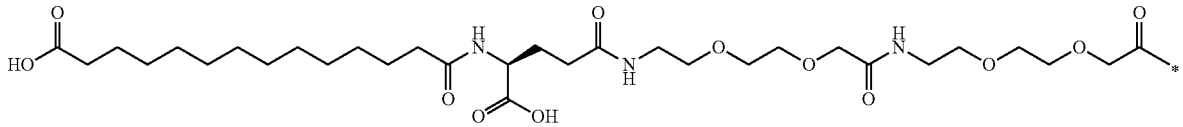

-continued

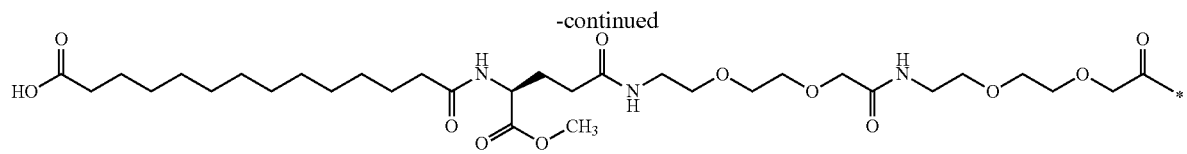

Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

In particular embodiments, the similarity coefficient is at least 0.80, preferably at least 0.85, more preferably at least 0.90, even more preferably at least 0.95, or most preferably at least 0.99.

In some embodiments the GLP-1 derivative comprises a GLP-1 peptide, wherein the GLP-1 peptide comprises a first K residue and a second K residue selected from the group consisting of i) a first K residue at a position corresponding to position 26 of GLP-1(7-37) (SEQ ID NO: 1) and a second K residue at a position corresponding to position 37 of GLP-1(7-37); and ii) a first K residue at a position corresponding to position 27 of GLP-1(7-37) (SEQ ID NO: 1) and a second K residue at a position corresponding to position T of GLP-1(7-37), where T is an integer in the range of 7-37; wherein the first K residue is designated $K^F$, and the second K residue is designated $K^T$;

wherein the GLP-1 peptide comprises a maximum of ten amino acid changes as compared to GLP-1(7-37);

wherein the GLP-1 derivative comprises a first and a second protracting moiety attached to $K^F$ and $K^T$, respectively, via a first and a second linker, respectively, wherein the first and the second protracting moiety is selected from Chem. C1 and Chem. C2:

HOOC—(CH$_2$)$_x$—CO—*      Chem. C1:

HOOC—C$_6$H$_4$—O—(CH$_2$)$_y$—CO—*      Chem. C2:

in which x is an integer in the range of 6-16, y is an integer in the range of 3-17; and the first and second linker comprises Chem. D5:

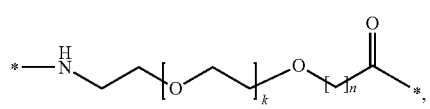

Chem. D5 wherein k is an integer in the range of 1-5, and n is an integer in the range of 1-5; or a pharmaceutically acceptable salt, amide, or ester thereof. In some embodiments the GLP-1 derivative comprises a GLP-1 peptide, wherein the GLP-1 peptide comprises a first K residue and a second K residue selected from the group consisting of i) a first K residue at a position corresponding to position 26 of GLP-1(7-37) (SEQ ID NO: 1) and a second K residue at a position corresponding to position 37 of GLP-1(7-37); and ii) a first K residue at a position corresponding to position 27 of GLP-1(7-37) (SEQ ID NO: 1) and a second K residue at a position corresponding to position T of GLP-1(7-37), where T is an integer in the range of 7-37; wherein the first K residue is designated $K^F$, and the second K residue is designated $K^T$; wherein the GLP-1 peptide comprises a maximum of ten amino acid changes as compared to GLP-1(7-37); wherein the GLP-1 derivative comprises a first and a second protracting moiety attached to $K^F$ and $K^T$, respectively, via a first and a second linker, respectively, wherein the first and the second protracting moiety is selected from Chem. 1 and Chem. 2:

HOOC—(CH$_2$)$_x$—CO—*      Chem. C1:

HOOC—C$_6$H$_4$—O—(CH$_2$)$_y$—CO—*      Chem. C2:

in which x is an integer in the range of 6-16, y is an integer in the range of 3-17; and the first and second linker comprises Chem. D5:

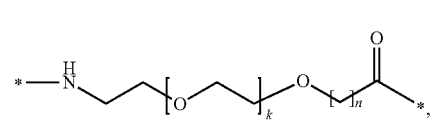

Chem. D5 wherein k is an integer in the range of 1-5, and n is an integer in the range of 1-5; or a pharmaceutically acceptable salt, amide, or ester thereof.

In some embodiments ($K^F$,$K^T$) are at positions corresponding to positions (26,37) of GLP-1(7-37) (SEQ ID NO: 1). In some embodiments ($K^F$,$K^T$) are at positions corresponding to positions (27,36) of GLP-1(7-37) (SEQ ID NO: 1).

In some embodiments the GLP-1 derivative comprises the protracting moiety Chem. C2. In some embodiments Chem. C2 is represented by Chem. C2a:

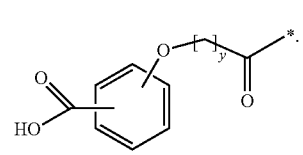

Chem. C2a

In some embodiments y of Chem. C2 or Chem. C2a is an odd number. In some embodiments y of Chem. 2 or Chem. 2a is an integer in the range of 9-11, such as 9, 10 or 11. In some embodiments Chem. C2 is represented by Chem. C2b, or Chem. C2c:

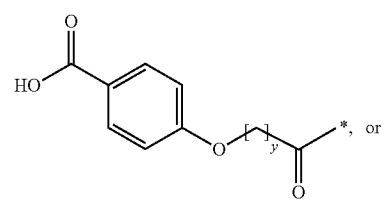

Chem. C2b

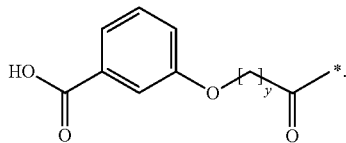

Chem. C2c

In some embodiments Chem. D5 is a first linker element. In some embodiments Chem. 5 is a first linker element. In some embodiments k of Chem. D5 is 1. In some embodiments n of Chem. D5 is 1. In some embodiments Chem. D5 is included m times, wherein m is an integer in the range of 1-10. In some embodiments m is 2. When m is not 1, then the Chem. D5 elements may be interconnected via amide bond(s).

In some embodiments the GLP-1 derivative further comprises a second linker element. In some embodiments the second linker element is a Glu di-radical. In some embodiments the second linker element is selected from Chem. E6, and/or Chem. E7:

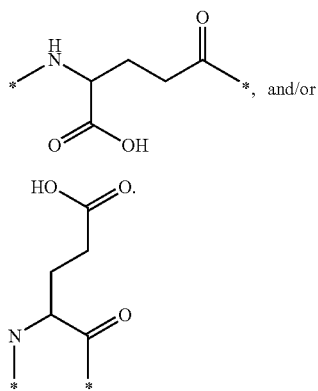

Chem. E6

, and/or

Chem. E7

In some embodiments the second linker element is Chem. E6. In some embodiments the Glu di-radical is included p times, wherein p is an integer in the range of 1-2, such as 1 or 2. In some embodiments the second linker element comprises the Glu di-radical which is a radical of L-Glu. In some embodiments the second linker element comprises one or more Glu di-radicals and one or more Chem. D5 elements are interconnected via amide bond(s). In some embodiments the linker consists of m times Chem. D5 and p times the Glu di-radical. In some embodiments (m,p) is (2,2) or (2,1). In some embodiments (m,p) is (2,1). In some embodiments the m Chem. D5 elements and the p Glu di-radicals are interconnected via amide bonds.

In some embodiments the linker and the protracting moiety are interconnected via an amide bond. In some embodiments the linker and the GLP-1 peptide are interconnected via an amide bond. In some embodiments the linker is attached to the epsilon-amino group of the first or the second K residue.

In some embodiments the GLP-1 derivative is semaglutide. Semaglutide may be prepared as disclosed in WO2006/097537, e.g. Example 4. Semaglutide may be referred to as N-ε26-[2-(2-[2-(2-[2-(2-[4-(17-Carboxyheptadecanoylamino)-4(S)-carboxybutyrylamino]ethoxy)ethoxy]acetylamino)ethoxy]ethoxy)acetyl][Aib8,Arg34]GLP-1-(7-37)peptide. Alternatively, semaglutide may be referred to as $N^{6.26}$-{18-[N-(17-carboxyheptadecanoyl)-L-γ-glutamyl]-10-oxo-3,6,12,15-tetraoxa-9,18-diazaoctadecanoyl}-[8-(2-amino-2-propanoic acid),34-L-arginine]human glucagon-like peptide 1(7-37) (WHO Drug Information Vol. 24, No. 1, 2010).

In some embodiments the GLP-1 derivative is Compound A which is $N^{ε26}${2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl}, $N^{ε37}$-{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl}[Aib$^8$,Arg$^{34}$,Lys$^{37}$]GLP-1(7-37)-peptide and has the following structure:

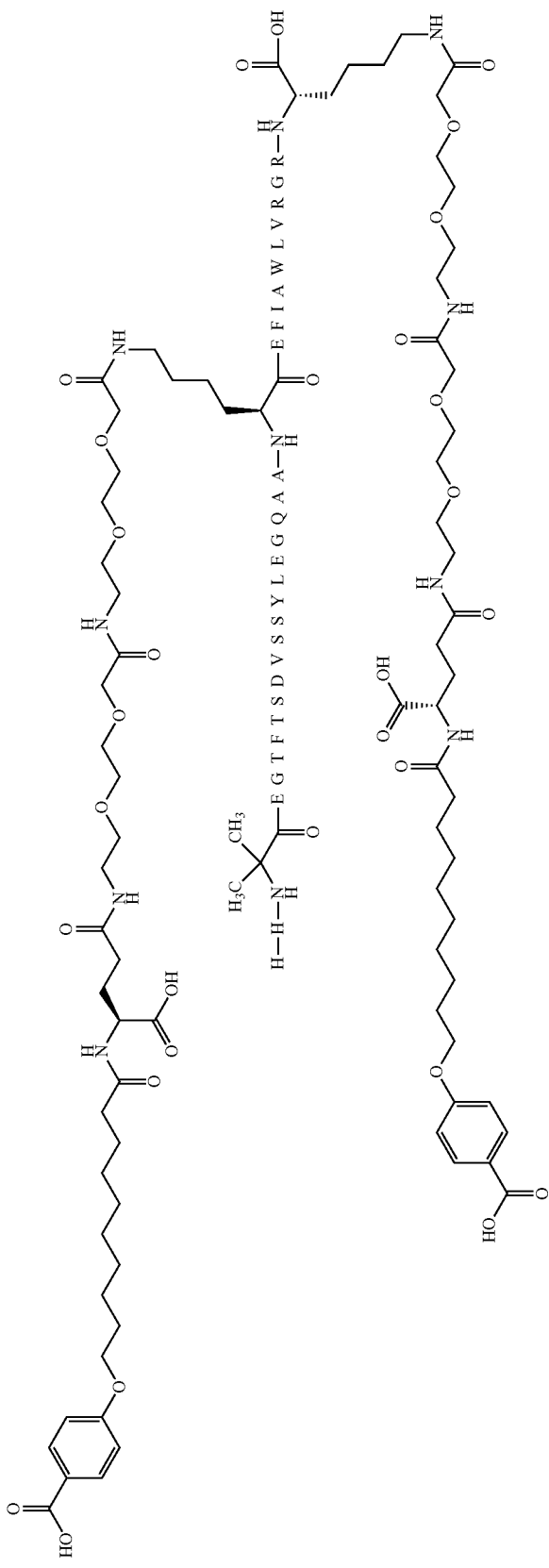

(the amino acid sequence of which, i.e. [Aib$^8$,Arg$^{34}$,Lys$^{37}$]GLP-1(7-37)-peptide, is shown in SEQ ID NO: 3). Compound A may be prepared as disclosed in WO2011/080103, e.g. Example 2.

In some embodiments the GLP-1 derivative is Compound B which is N$^{ε27}$-[2-[2-[2-[[2-[2-[2-[[(4S)-4-carboxy-4-[10-(4-carboxyphenoxy)decanoylamino]butanoyl]amino]ethoxy]ethoxy]acetyl] amino]ethoxy]ethoxy]acetyl], N$^{ε36}$-[2-[2-[2-[[2-[2-[2-[[(4S)-4-carboxy-4-[10-(4-carboxyphenoxy) decanoylamino]butanoyl]amino]ethoxy]ethoxy]acetyl]amino]ethoxy]ethoxy]acetyl][Aib8,Glu22,Arg26,Lys27,Glu30,Arg34,Lys36]-GLP-1-(7-37)-peptidyl-Glu-Gly and has the following structure:

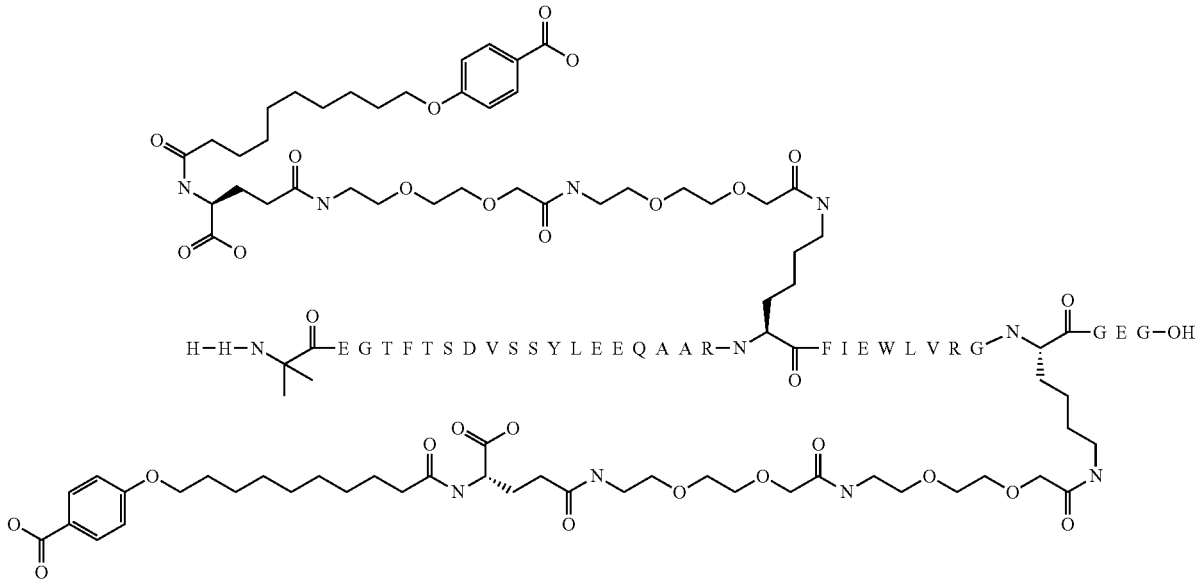

(the amino acid sequence of which is shown in SEQ ID NO: 4). Compound B may be prepared as disclosed in WO2012/140117, e.g. Example 31. Compound B may also be illustrated as follows

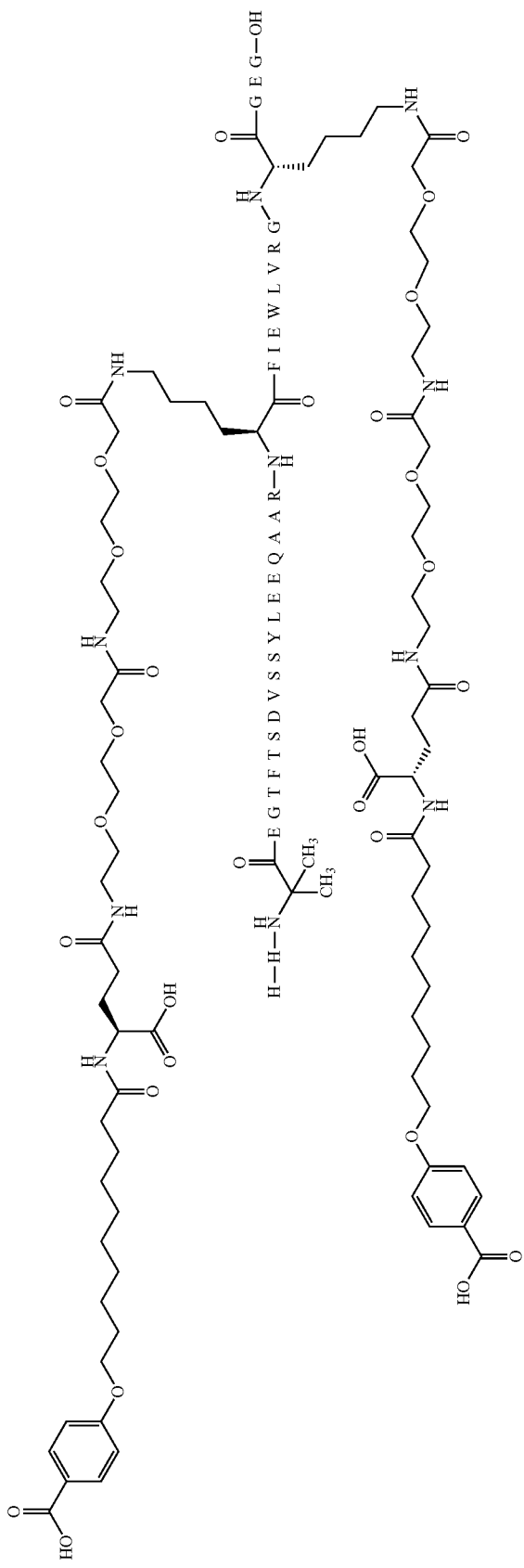

(the amino acid sequence of which is shown in SEQ ID NO: 4).

In some embodiments the GLP-1 agonist is a GLP-1 derivative (e.g. a derivative of a GLP-1 peptide) acylated with a side chain on the epsilon-amino group of a lysine at each of positions 36 and 37;

wherein each side chain individually comprises a protractor of formula:

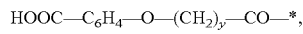

Chem. 1:

where y is an integer in the range of 8-11, attached to epsilon-amino group of a lysine at position 36 and 37; and wherein the protractor is attached to the epsilon-amino group via a linker comprising i) gGlu of the formula:

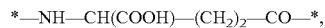

Chem. 3:

and ii) a moiety of the formula:

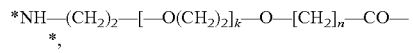

Chem. 5:

wherein k is an integer in the range of 1-5, and n is an integer in the range of 1-5;

or a pharmaceutically acceptable salt, amide, or ester thereof.

In some embodiments, in the GLP-1 derivative of the invention, the linker, protractor, and peptide are connected via amide bonds at*. In some embodiments gGlu of the linker is connected to the protractor via amide bonds at*. In some embodiments gGlu of the linker is connected to the moiety of Chem. 5 via amide bonds at*. In some embodiments the moiety of Chem. 5 of the linker is connected to the peptide via amide bonds at*. In some embodiments the moiety of the formula defined by Chem. 5 is "OEG", i.e. n=k=1. In some embodiments the linker is "*-gGlu-OEG-OEG-**" connected to the protractor at * and connected to the peptide at**. In some embodiments the protractor has y=10 and is in para configuration. In some embodiments the protractor has y=9 and is in para configuration. In some embodiments the protractor has y=9 or y=10 and is in meta configuration.

In some embodiments the GLP-1 derivative comprises Formula II (SEQ ID 7):

Formula II: Xaa7-Xaa8-Glu-Gly-Thr-Phe-Thr-Ser-Asp-Xaa16-Ser-Xaa18-Xaa19-Xaa20-Glu-Xaa22-Xaa23-Ala-Xaa25-Xaa26-Xaa27-Phe-Ile-Xaa30-Xaa31-Leu-Xaa33-Xaa34-Xaa35-Lys36-Lys37 (SEQ ID NO: 5), wherein Xaa7 is L-histidine, (S)-2-Hydroxy-3-(1H-imidazol-4-yl)-propionic acid, D-histidine, desamino-histidine (desH), Nα-acetyl-histidine, or Nα-formyl-histidine;

Xaa8 is Ala, Ser, Aib, (1-aminocyclopropyl) carboxylic acid, or (1-aminocyclobutyl) carboxylic acid;

Xaa16 is Val or Leu;
Xaa18 is Ser or Arg;
Xaa19 is Tyr or Gln;
Xaa20 is Leu or Met;
Xaa22 is Gly or Glu;
Xaa23 is Gln, Glu, or Arg;
Xaa25 is Ala or Val;
Xaa26 is Arg or Lys;
Xaa27 is Glu or Leu;
Xaa30 is Ala, or Glu;
Xaa31 is Trp or His
Xaa33 is Val or Arg;
Xaa34 is Arg, Lys, His, Asn, or Gln; and
Xaa35 is Gly or Aib.

In some embodiments the GLP-1 derivative is a GLP-1 derivative of Formula II (SEQ ID 7), wherein Xaa7 is His; Xaa8 is Aib; Xaa16 is Val; Xaa18 is Ser; Xaa19 is Tyr; Xaa20 is Leu; Xaa22 is Gly or Glu; Xaa23 is Gln; Xaa25 is Ala; Xaa26 is Arg; Xaa27 is Glu; Xaa30 is Ala or Glu; Xaa31 is Trp; Xaa33 is Val; Xaa34 is Arg or Gln; and Xaa35 is Gly.

In some embodiments the GLP-1 derivative is a GLP-1 derivative of Formula II (SEQ ID 7), wherein Xaa7 is His; Xaa8 is Aib; Xaa16 is Val; Xaa18 is Ser; Xaa19 is Tyr; Xaa20 is Leu; Xaa22 is Glu; Xaa23 is Gln; Xaa25 is Ala; Xaa26 is Arg; Xaa27 is Glu; Xaa30 is Ala; Xaa31 is Trp; Xaa33 is Val; Xaa34 is Arg; and Xaa35 is Gly.

In some embodiments the GLP-1 derivative is Compound C which is N{Epsilon-36}-[2-[2-[2-[[2-[2-[2-[[(4S)-4-carboxy-4-[11-(4-carboxyphenoxy)undecanoylamino]butanoyl]amino] ethoxy]ethoxy]acetyl]amino]ethoxy]ethoxy] acetyl],N{Epsilon-37}-[2-[2-[2-[[2-[2-[2-[[(4S)-4-carboxy-4-[11-(4-carboxyphenoxy)undecanoylamino]butanoyl] amino]ethoxy]ethoxy]acetyl]amino]ethoxy]ethoxy]acetyl]-[Aib8,Glu22,Arg26,Arg34,Lys36,Lys37]-GLP-1-(7-37)-peptide and has the following structure:

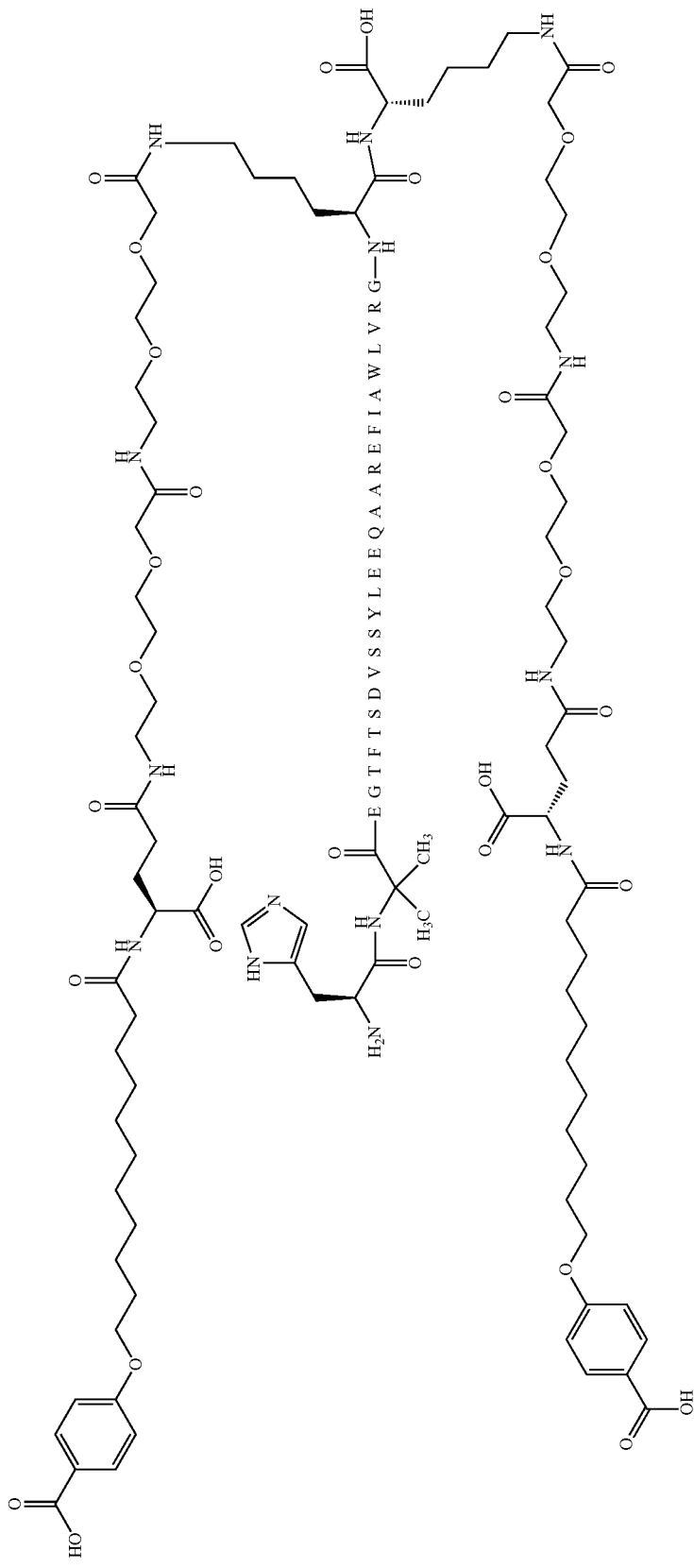

(the amino acid sequence of which is shown in SEQ ID NO: 6). Compound C may be prepared as disclosed in Example 1 of WO2015/155151.

In some embodiments the GLP-1 derivative is Compound D which is N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide and has the following structure:

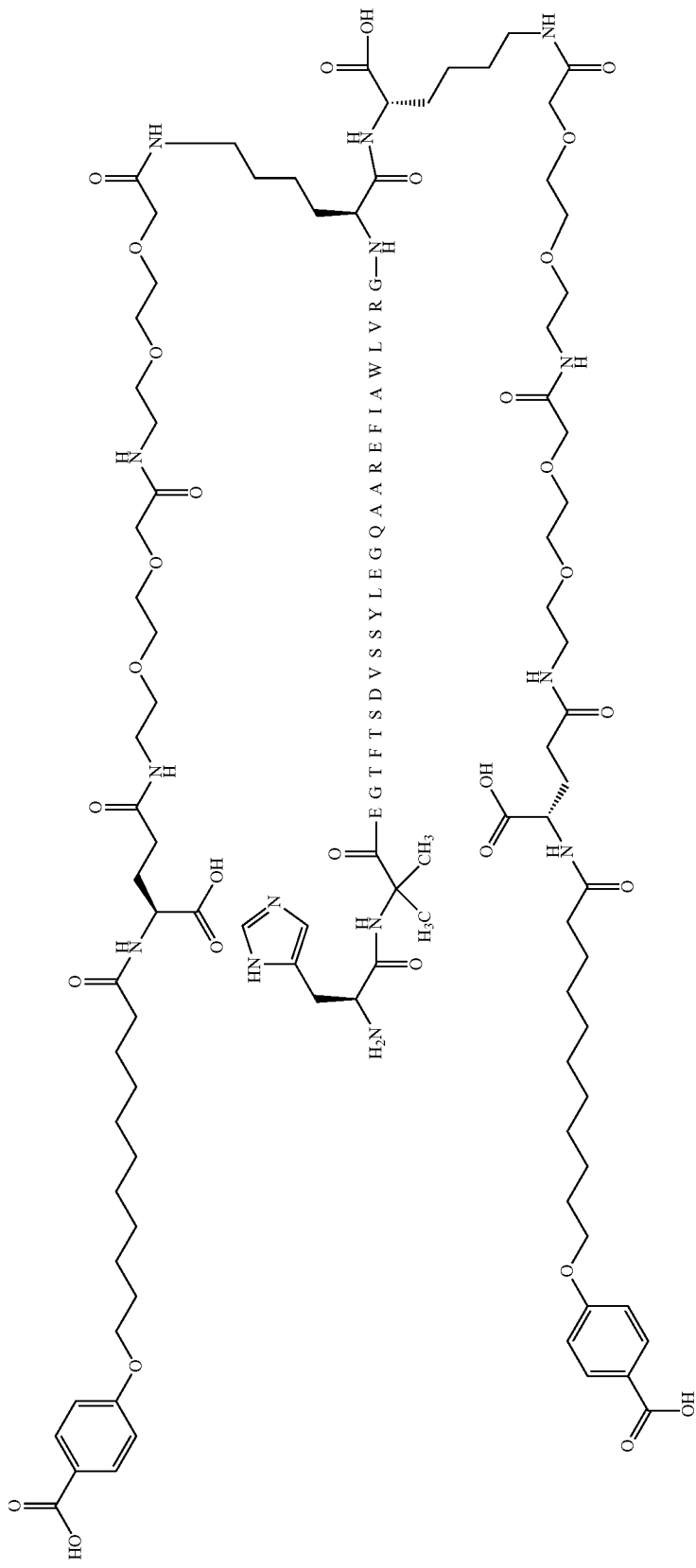

(the amino acid sequence of which is shown in SEQ ID NO: 7. Compound D may be prepared as disclosed in Example 2 of WO2015/155151. In some embodiments Compound C and Compound D may be prepared according to other methods known by a person skilled in the art.

In some embodiments the GLP-1 derivative is Compound E which is N{Epsilon-36}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide In some embodiments the GLP-1 peptide or the derivative thereof is in the form of a salt, ester or amide thereof.

A non-limiting list of examples of GLP-1 peptides or derivatives thereof for use in the present invention may be found in WO 2006/097537, WO 2011/080103, WO2012/140117, and/or PCT/EP2015/057442. Methods for preparation of GLP-1 peptides of the present invention can for example be found in WO2006/097537, WO2011/080103, WO2012/140117, or PCT/EP2015/057442. Methods for preparation of such GLP-1 peptides as well as assays for characterizing such GLP-1 peptides, such as physical and chemical stability as well as potency and $T_{1/2}$ are provided in WO2006/097537, WO2011/080103, WO2012/140117,

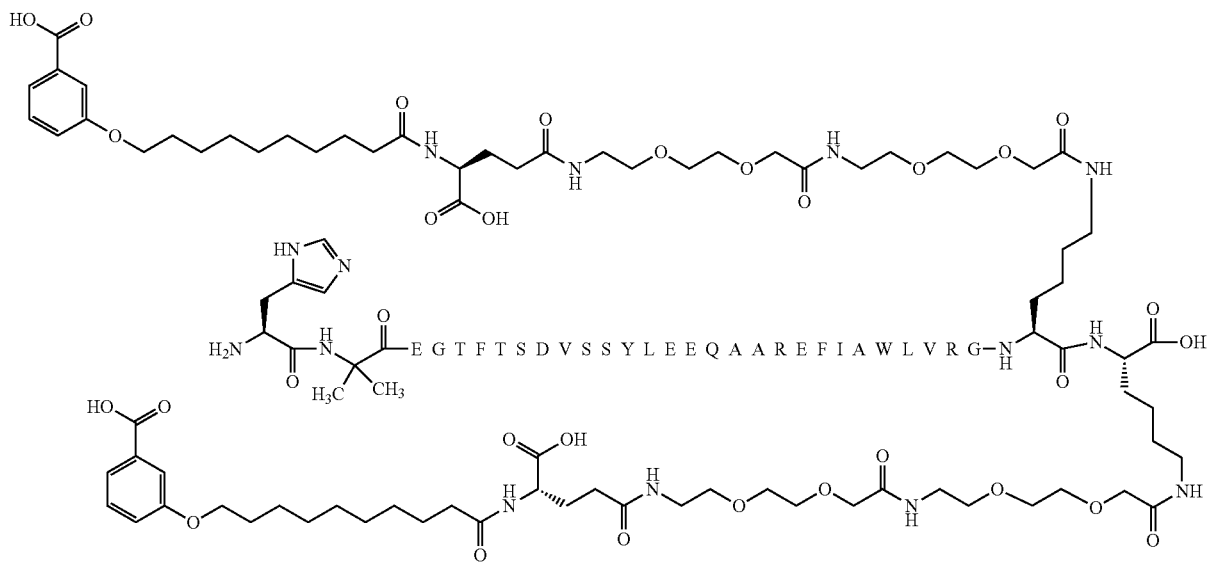

(the amino acid sequence of which is shown in SEQ ID NO: 8). Compound E may be prepared as disclosed in e.g. WO2012/140117 or Example 35 of WO2015/155151.

In some embodiments the GLP-1 derivative is selected from the group consisting of semaglutide, Compound A, Compound B, Compound C, Compound D, and Compound E. In some embodiments the GLP-1 derivative is selected from the group consisting of semaglutide, Compound A, Compound B, and Compound E.

The GLP-1 derivatives may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of GLP-1 derivatives may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO 2009/030738 on p. 116-118.

and PCT/EP2015/057442. Compound E may be prepared as disclosed in e.g. WO2012/140117 or Example 2 of PCT/EP2015/057442.

In some embodiments the GLP-1 peptide or the derivative thereof has a plasma half-life in humans of at least 60 hours. In some embodiments the GLP-1 peptide or the derivative thereof has plasma half-life in humans of at least 60 hours, such as at least 100 hours, or at least 160 hours. In some embodiments the GLP-1 peptide or the derivative thereof has plasma half-life in humans of at least 1 day, at least 36 hours or at least 2 days.

SGLT2 Inhibitors

In some embodiments the compositions of the invention comprise an SGLT2 inhibitor. In some embodiments the SGLT2 inhibitor is also an SGLT1 inhibitor. SGLT2 and SGLT1 inhibitors are compounds with the capacity to inhibit the sodium glucose linked transporter. In some embodiments the SGLT2 inhibitor is a glucopyranosyl-substituted benzene derivative. In some embodiments the SGLT2 inhibitor is selected from the group consisting of dapagliflozin, empagliflozin, canagliflozin, ertugliflozin, sotagliflozin, Ipragliflozin, tofogliflozin, luseogliflozin, bexagliflozin, and remogloflozin, In some embodiments the SGLT2 inhibitor is dapagliflozin, In some embodiments the SGLT2 inhibitor is empagliflozin, In some embodiments the SGLT2 inhibitor is canagliflozin, In some embodiments the SGLT2 inhibitor is ertugliflozin, In some embodiments the SGLT2 inhibitor is sotagliflozin, In some embodiments the SGLT2 inhibitor is ipragliflozin, In some embodiments the SGLT2 inhibitor is tofogliflozin, In some embodiments the SGLT2 inhibitor is luseogliflozin, In some embodiments the SGLT2 inhibitor is bexagliflozin, In some embodiments the SGLT2 inhibitor is remogloflozin. SGLT2 inhibitors may be prepared according to methods known in the art, for example as shown in WO 2006/120208 WO 2007/031548, or WO2008/002824.

The term "SGLT2 inhibitor" as used herein relates to a compound which provides an inhibitory effect on the sodium-glucose transporter 2 (SGLT2), such as the human SGLT2. In some embodiments inhibitory effect on the human SGLT2, measured as IC50, of the SGLT2 inhibitor is below 1000 nM, such as below 100 nM or below 50 nM. In some embodiments IC50 values of the SGLT2 inhibitor is at least 0.01 nM, such as at least 0.1 nM. Methods for determining inhibitory effect on human SGLT2 are known in the art, e.g. page 23-24 of WO2007/093610. In some embodiments the SGLT2 inhibitor is in the form of a pharmaceutically acceptable salt, hydrate and/or solvate thereof. In some embodiments the SGLT2 inhibitor is in an amorphous form. In some embodiments the SGLT2 inhibitor is in a crystalline form, for example of its pharmaceutically acceptable salt, hydrate and/or solvate.

Dapagliflozin

In some embodiments the compositions of the invention comprise the SGLT2 inhibitor dapagliflozin. In some embodiments the structure of dapagliflozin is as shown in formula (II):

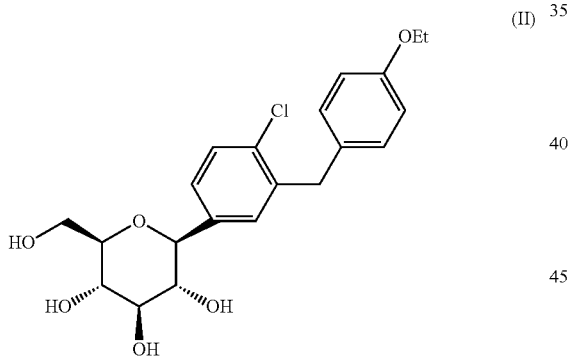

or a stereoisomer thereof. In some embodiments dapagliflozin is in the form of a pharmaceutically acceptable salt, an ester or a solvate thereof. The ester may be a prodrug ester of dapagliflozin, such as an in vivo cleavable ester. A pharmaceutically-acceptable ester may be cleaved in the human or animal body to produce the parent acid (e.g. where said ester is methoxymethyl) or hydroxy group (e.g. where said ester is an acetyl ester). The solvate may comprise or consist of a propylene glycol solvate of dapagliflozin, such as dapagliflozin propylene glycol (1:1). In some embodiments dapagliflozin is in the form its propylene glycol solvate hydrate (1:1:1). In some embodiments propylene glycol is in the (S) form, the (R) form, or a mixture thereof. In some embodiments propylene glycol is in the (S) form. In some embodiments dapagliflozin is administered at a dose from 0.5 to 200 mg/day, such as 3-20 mg/day, 5 mg/day or 10 mg/day.

Empagliflozin

In some embodiments the compositions of the invention comprise the SGLT2 inhibitor empagliflozin. In some embodiments the structure of empagliflozin is as shown in formula (III):

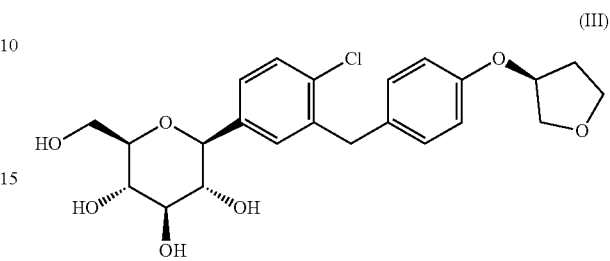

or a stereoisomer thereof. In some embodiments empagliflozin is in the form of a pharmaceutically acceptable salt, an ester or a solvate thereof. The ester may be a prodrug ester of empagliflozin, such as an in vivo cleavable ester. A pharmaceutically-acceptable ester may be cleaved in the human or animal body to produce the parent acid (e.g. where said ester is methoxymethyl) or hydroxy group (e.g. where said ester is an acetyl ester). In some embodiments the composition comprises empagliflozin in an amount of 0.5-200 mg, such as 5-50 mg. In some embodiments the composition comprises empagliflozin in an amount of 10 mg or 25 mg. In some embodiments empagliflozin is administered at a dose of 0.5-200 mg/day, such as 5-50 mg/day. In some embodiments empagliflozin is administered at a dose of 10 mg/day or 25 mg/day.

Absorption Enhancer

The method or use of the present invention may comprise an enhancer. In some embodiments the enhancer is water soluble. In some embodiments the term "enhancer" refers to a compound which increases the bioavailability of the GLP-1 peptide of the composition following oral administration. Accordingly, in some embodiments the enhancer is a bioavailability enhancer. In some embodiments the weight percentage of the enhancer is at least 60% (w/w), such as at least 70% (w/w) or at least 75% (w/w), of the total weight of the composition.

In some embodiments the enhancer is a medium chain fatty acid or a salt thereof and has a carbon chain length of from about 4 to about 20 carbon atoms. In some embodiments the enhancer is a salt of capric acid, such as sodium caprate. In some embodiments the weight percentage of said medium chain fatty acid, such as a salt of capric acid (e.g. sodium caprate), is at least 60% (w/w), such as at least 70% (w/w) or at least 75% (w/w), of the total weight of the composition. In some embodiments the amount of said medium chain fatty acid, such as a salt of capric acid (e.g. sodium caprate), in the composition is at least 2.0 mmol, such as at least 2.5 mmol or at least 3.5 mmol, in one dosage unit. In some embodiments the amount of a salt of capric acid, such as sodium caprate, in the composition is at least 300 mg, at least 400 mg, or at least 500 mg.

In some embodiments the enhancer is a salt of N-(8-(2-hydroxybenzoyl)amino)caprylic acid. In some embodiments the enhancer is an absorption enhancer. The structural formula of N-(8-(2-hydroxybenzoyl)amino)caprylate is shown in formula (I).

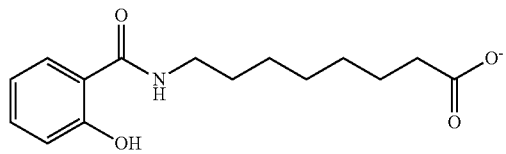

(I)

In some embodiments the salt of N-(8-(2-hydroxybenzoyl)amino)caprylic acid is in the caprylic acid form and/or the caprylate form. In some embodiments the salt of N-(8-(2-hydroxybenzoyl)amino)caprylic acid comprises one monovalent cation, two monovalent cations or one divalent cation. In some embodiments the salt of N-(8-(2-hydroxybenzoyl) amino) caprylic acid is selected from the group consisting of the sodium salt, potassium salt and calcium salt of N-(8-(2-hydroxybenzoyl)amino)caprylic acid. Salts of N-(8-(2-hydroxybenzoyl)amino)caprylate may be prepared using the method described in e.g. WO96/030036, WO00/046182, WO01/092206 or WO2008/028859. The salt of N-(8-(2-hydroxybenzoyl)amino)caprylic acid may be crystalline and/or amorphous. In some embodiments the enhancer comprises the anhydrate, monohydrate, dihydrate, trihydrate, a solvate or one third of a hydrate of the salt of N-(8-(2-hydroxybenzoyl)amino) caprylic acid as well as combinations thereof. In some embodiments the enhancer is a salt of N-(8-(2-hydroxybenzoyl)amino)caprylic acid as described in WO2007/121318. In some embodiments the enhancer is sodium N-(8-(2-hydroxybenzoyl)amino)caprylate (referred to as "SNAC" herein), also known as sodium 8-(salicyloylamino) octanoate. In some embodiments the weight percentage of the salt of N-(8-(2-hydroxybenzoyl) amino)caprylic acid, such as SNAC, is at least 60% (w/w), such as at least 70% (w/w) or at least 75% (w/w), of the total weight of the composition. In some embodiments the weight percentage of the salt of N-(8-(2-hydroxybenzoyl)amino) caprylic acid, such as SNAC, is 50-90% (w/w) of the total weight of the composition. In some embodiments the amount of the salt of N-(8-(2-hydroxybenzoyl) amino) caprylic acid in the composition is in the range of 0.2-5 mmol, such as 0.6-3.5 mmol. In some embodiments the amount of the salt of N-(8-(2-hydroxybenzoyl) amino) caprylic acid in the composition is at least 0.6 mmol. In some embodiments the amount of SNAC in the composition is in the range of 20-1000 mg, such as 50-800 mg or 100-600 mg. In some embodiments the amount of SNAC is 100-500 mg, such as 200-400 mg or 300 mg. In some embodiments the molar ratio between GLP-1 peptide and enhancer in the composition is less than 10, such as less than 5 or less than 1.

Solid Compositions

The method or use of the invention comprises a composition comprising a GLP-1 peptide and optionally an enhancer. In some embodiments the composition is in the form of a solid dosage form. The solid dosage form for oral administration may be selected from the group consisting of capsules, tablets, powders and/or granules. In some embodiments the composition is in the form of a tablet. In some embodiments the composition is in the form of a capsule. In some embodiments the composition is in the form of a sachet. In some embodiments the composition comprises granules which have been manufactured by dry granulation or wet granulation. In some embodiments the composition comprises granules which have been manufactured by roller compaction. In some embodiments the moldings from the roller compaction process are comminuted into granules. In some embodiments the term "granulate" refers to one or more granules. In some embodiments the term "granule" refers to particles gathered into larger particles.

In some embodiments the term "composition" as used herein refers to one dosage unit.

In some embodiments the composition or granule comprises one or more pharmaceutically acceptable excipients. The term "excipient" as used herein broadly refers to any component other than the active therapeutic ingredient(s) (also referred to in the art as drug substance or active pharmaceutical ingredient(s)). The excipient may be an inert substance, which is inert in the sense that it substantially does not have any therapeutic and/or prophylactic effect per se. The excipient may serve various purposes, e.g. as a enhancer, absorption enhancer, vehicle, filler (also known as diluents), binder, lubricant, glidant, disintegrant, crystallization retarders, acidifying agent, alkalizing agent, preservative, antioxidant, buffering agent, chelating agent, complexing agents, surfactant agent, emulsifying and/or solubilizing agents, sweetening agents, wetting agents stabilizing agent, colouring agent, flavouring agent, and/or to improve administration, and/or absorption of the active substance. A person skilled in the art may select one or more of the aforementioned excipients with respect to the particular desired properties of the solid oral dosage form by routine experimentation and without any undue burden. The amount of each excipient used may vary within ranges conventional in the art. Techniques and excipients which may be used to formulate oral dosage forms are described in Handbook of Pharmaceutical Excipients, 6th edition, Rowe et al., Eds., American Pharmaceuticals Association and the Pharmaceutical Press, publications department of the Royal Pharmaceutical Society of Great Britain (2009); and Remington: the Science and Practice of Pharmacy, 21th edition, Gennaro, Ed., Lippincott Williams & Wilkins (2005).

In some embodiments the composition or granule comprises a filler, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), other cellulose derivatives, sucrose, sorbitol, mannitol, dextrins, dextrans, maltodextrins, dextrose, fructose, kaolin, mannitol, sorbitol, sucrose, sugar, starches or modified starches (including potato starch, maize starch and rice starch), calcium phosphate (e.g. basic calcium phosphate, calcium hydrogen phosphate, dicalcium phosphate hydrate), calcium sulphate, calcium carbonate, or sodium alginate. In some embodiments the filler is microcrystalline cellulose, such as Avicel PH 101.

In some embodiments the composition or granule comprises a binder, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), hydroxypropylcellulose, L-hydroxypropylcellulose (low-substituted), hypromellose (HPMC) (e.g. Methocel E, F and K, Metolose SH of Shin-Etsu, Ltd, such as, e.g., the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, ethylcellulose, sodium carboxymethylcellulose, other cellulose derivatives, sucrose, dextrins, maltodextrins, starches or modified starches (including potato starch, maize starch and rice starch), calcium lactate, calcium carbonate, acacia, sodium alginate, agar, carrageenan, gelatin, guar gum, pectin, PEG, or povidone. In some embodiments the binder is povidone, such as povidone K 90.

In some embodiments the composition or granule comprises a disintegrant, such as alginic acid, alginates, microcrystalline cellulose, hydroxypropyl cellulose, other cellulose derivatives, croscarmellose sodium, crospovidone, polacrillin potassium, sodium starch glycolate, starch, pregelatinized starch, or carboxymethyl starch (e.g. Primogel® and Explotab®).

In some embodiments the composition or granule comprises a lubricant, such as stearic acid, magnesium stearate, calcium stearate or other metallic stearate, talc, waxes, glycerides, light mineral oil, glyceryl behenate, hydrogenated vegetable oils, sodium stearyl fumarate, polyethylene glycols, alkyl sulfates, or sodium benzoate. In some embodiments the composition or granule comprises a lubricant, such as magnesium silicate, talc, or colloidal silica. In some embodiments the lubricant is magnesium stearate.

In some embodiments the composition or granule comprises one or more excipients selected from crystallization retarders, such as Povidone, etc.; solubilizing agents (also known as surfactants), such as anionic surfactants (e.g. Pluronic or Povidone), cationic surfactants, nonionic surfactants, and/or zwitterionic surfactants; colouring agents, including dyes and pigments, such as Iron Oxide Red or Yellow, titanium dioxide, and/or talc; and/or pH control agents, such as citric acid, tartaric acid, fumaric acid, sodium citrate, dibasic calcium phosphate, and/or dibasic sodium phosphate.

In some embodiments the composition comprises at least 60% (w/w) enhancer, less than 10% (w/w) binder, 5-40% (w/w) filler, and less than 10% (w/w) lubricant. In some embodiments the enhancer is a salt of N-(8-(2-hydroxybenzoyl)amino)caprylic acid and the composition comprises a first granule comprising GLP-1 peptide and no a salt of N-(8-(2-hydroxybenzoyl)amino)caprylic acid and a second granule comprising a salt of N-(8-(2-hydroxybenzoyl)amino)caprylic acid and no GLP-1 peptide.

The composition may comprise one or more coatings, which may be prepared according to methods well known in the art.

Manufacture

The composition for use in the present invention may be prepared as is known in the art. In some embodiments the composition may be granulated prior to being compressed into tablets. In some embodiments the granules are manufactured by dry granulation, such as by roller compaction. In some embodiments the moldings from the roller compactions process are comminuted into granules. The composition may comprise one or more intragranular parts and an extragranular part, wherein the intragranular parts have been granulated, and wherein the extragranular part has been added after granulation. A first intragranular part may comprise the GLP-1 peptide and one or more excipients, and a second intragranular part may comprise the enhancer and optionally one or more excipients. A first intragranular part may comprise the GLP-1 peptide, filler and/or a binder and a second intragranular part may comprise the enhancer, lubricant and/or filler. In some embodiments the first intragranular part comprises the GLP-1 peptide, microcrystalline cellulose and/or povidone and the second intragranular part comprises the enhancer, magnesium stearate and/or microcrystalline cellulose. The extragranular part may comprise a lubricant. In some embodiments the extragranular part comprises magnesium stearate.

To prepare a dry blend of tabletting material, the various components are weighed, optionally delumped and then combined. The mixing of the components may be carried out until a homogeneous blend is obtained.

In some embodiments at least a part of the composition is dry granulated or wet granulated. A granulate may be produced in a manner known to a person skilled in the art, for example by dry granulation techniques in which the pharmaceutically active agent and/or enhancers are compacted with the excipients to form relatively large moldings, for example slugs or ribbons, which are comminuted by grinding, and the ground material serves as the tabletting material to be later compressed into tablets. Suitable equipment for dry granulation includes but is not limited to roller compaction equipment from Gerteis, such as Gerteis MINI-PACTOR. In some embodiments the granulate is prepared by roller compaction. In some embodiments the moldings from the roller compactions process are comminuted into granules. Alternatively, a granulate can be obtained by wet granulation which may be carried out by mixing the pharmaceutically active agent dissolved in water with a dry blend of the enhancers and optionally one or more excipients followed by drying of the granulate.

To compress the tabletting material into a solid oral dosage form, for example a tablet, a tablet press may be used. In a tabletting press, the tabletting material is filled (e.g. force fed or gravity fed) into a die cavity. The tabletting material is then compressed by a punch with pressure. Subsequently, the resulting compact, or tablet is ejected from the tabletting press. The above mentioned compression process is subsequently referred to herein as the "compression process". Suitable tablet presses include, but are not limited to, rotary tablet presses and eccentric tablet presses. Examples of tablet presses include, but are not limited to, the Fette 102i (Fette GmbH), the Korsch XL100, the Korsch PH 106 rotary tablet press (Korsch AG, Germany), the Korsch EK-O eccentric tabletting press (Korsch AG, Germany) and the Manesty F-Press (Manesty Machines Ltd., United Kingdom). In some embodiments the tablet is prepared by exerting a compression force in the range of 3-20 kN or 5-25 kN.

Functional Features

Oral Bioavailability

In some embodiments the solid pharmaceutical compositions of the invention provide an improved oral bioavailability of the GLP-1 agonist and/or dapagliflozin. Generally, the term bioavailability refers to the fraction of an administered dose of the drug substance (such as a GLP-1 peptide or a derivative thereof) that reaches the systemic circulation unchanged. By definition, when a drug substance is administered intravenously, its bioavailability is 100%. However, when the drug substance is administered via other routes (such as orally), its bioavailability decreases (due to degradation and/or incomplete absorption and first-pass metabolism). Knowledge about bioavailability is important when calculating dosages for non-intravenous routes of administration of a drug substance. A plasma concentration versus time plot is made after both oral and intravenous administration. The absolute bioavailability is the (AUC-oral divided by dose), divided by (AUC-intravenous divided by dose).

Indications

The composition for use in the present invention is for use in as a medicament. In some embodiments the composition is for use in the treatment or prevention of diabetes and/or obesity.

It will be appreciated that the composition or the GLP-1 peptide for use as an oral pharmaceutical product (i.e. medicament), may be described as a method of administration or alternatively be described as use of a composition in the manufacture of an oral pharmaceutical product. It will be appreciated that the method of administration described herein may alternatively be described as a composition for use as an oral pharmaceutical product, alternatively use of a composition in the manufacture of an oral pharmaceutical product. The method of administration described herein may alternatively be described as a GLP-1 peptide for use as an oral pharmaceutical product, alternatively use of a GLP-1 peptide in the manufacture of an oral pharmaceutical product. Analogously, the use of a GLP-1 peptide described herein may alternatively be described as a method of administration or use of a GLP-1 peptide in the manufacture of an oral pharmaceutical product. In some embodiments the terms "dosing regimen" and "method of administration" are used interchangeably herein. Herein, in some embodiments the term "use" includes a composition for use, e.g. "use in medicine" includes a "composition for use in medicine". In some embodiments the term "method" as used herein includes a method of administration, e.g. a method of oral administration.

The method of administration of the invention comprises oral therapy. In some embodiments the method comprises treatment or prevention of diabetes and/or obesity.

In some embodiments the method or use comprises (e.g. the GLP-1 peptide of the invention may be used for the following medical treatments):

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1c;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying.

In some embodiments the indication is (i). In some embodiments the indication is (ii). In a still further particular aspect the indication is (iii). In some embodiments the indication is type 2 diabetes and/or obesity.

In some embodiments the method or use comprises prevention, treatment, reduction and/or induction in one or more diseases or conditions defined herein. In some embodiments the indication is (i) and (iii). In some embodiments the indication is (ii) and (iii). In some embodiments the inven-tion comprises administration of an effective amount of a GLP-1 peptide. In some embodiments the invention relates to administration of an effective amount of a GLP-1 peptide.

In some embodiments, as used herein, specific values given in relation to numbers or intervals may be understood as the specific value or as about the specific value. In some embodiments the term "about" when used herein in relation to a number refers to said number ±10%.

EMBODIMENTS OF THE INVENTION

The following are non-limiting embodiments of the invention:

1. A solid composition for oral administration comprising
   (i) a GLP-1 derivative and dapagliflozin, or
   (ii) a GLP-1 derivative and a salt of NAC in combination with an SGLT2 inhibitor.

2. The composition according to any one of the preceding embodiments, wherein said SGLT2 inhibitor is empagliflozin.

3. A solid composition comprising a GLP-1 derivative and dapagliflozin.

4. The composition according to any one of the preceding embodiments, wherein said composition is for oral administration.

5. A solid composition for oral administration comprising a GLP-1 derivative and second active ingredient, wherein said second active ingredient inhibits glucose reuptake via the SGLT2 receptor and increases permeability of said GLP-1 derivative through a cellular mono layer.

6. The composition according to any one of the preceding embodiments, wherein said composition further comprises an absorption enhancer.

7. The composition according to any one of the preceding embodiments, wherein said absorption enhancer is a salt of NAC, such as SNAC.

8. The composition according any one of the preceding embodiments, wherein said GLP-1 derivative is selected from the group consisting of semaglutide, Compound A, Compound B, Compound C, Compound D, and Compound E.

9. A solid composition comprising dapagliflozin and SNAC.

10. The composition according to any one of the preceding embodiments, wherein said composition further comprises a GLP-1 peptide.

11. The composition according to the preceding embodiment, wherein said GLP-1 peptide is a GLP-1 derivative, such as selected from the group consisting of semaglutide, Compound A, Compound B, Compound C, Compound D, and Compound E.

12. The composition according to any one of the preceding embodiments, wherein said GLP-1 peptide or said GLP-1 derivative has a size of no more than 12 kDa.

13. The composition according to any one of the preceding embodiments, wherein said GLP-1 peptide or said GLP-1 derivative comprises 10 amino acid modifications or less relative to human GLP-1.

14. The composition according to any one of the preceding embodiments, wherein said GLP-1 peptide or said GLP-1 derivative comprises 10 amino acid substitutions or less relative to human GLP-1.

15. The composition according to any one of the preceding embodiments, wherein said GLP-1 peptide or said GLP-1 derivative has a plasma half-life in humans of at least 60 hours.

16. The composition according to any one of the preceding embodiments, wherein said GLP-1 peptide, GLP-1 derivative, and/or dapagliflozin is in the form of a pharmaceutically acceptable salt, ester or solvate thereof.

17. The composition according to any one of the preceding embodiments, wherein said GLP-1 peptide or said GLP-1 derivative is in the form of a pharmaceutically acceptable salt or ester thereof.

18. The composition according to any one of the preceding embodiments, wherein said SGLT2 inhibitor is in the form of a pharmaceutically acceptable salt, ester or solvate thereof.

19. The composition according to any one of the preceding embodiments, wherein said dapagliflozin is in the form of a pharmaceutically acceptable salt, ester or solvate thereof.

20. The composition according to any one of the preceding embodiments, wherein said dapagliflozin is in the form of a dapagliflozin propylene glycol solvate.

21. The composition according to any one of the preceding embodiments, wherein said dapagliflozin is in the form of dapagliflozin propylene glycol hydrate (1:1:1).

22. The composition according to any one of the preceding embodiments, wherein said propylene glycol is in the form of the (R) or (S) stereoisomer or a mixture thereof.

23. The composition according to any one of the preceding embodiments, wherein said composition comprises one or more additional pharmaceutically acceptable excipients.

24. The composition according to any one of the preceding embodiments, wherein said composition is in the form of a tablet, a capsule or a sachet.

25. The composition according to any one of the preceding embodiments, wherein the dosage of said composition administered is in the range of 10-1500 mg or 200-1000 mg.

26. The composition according to any one of the preceding embodiments, wherein the dosage of dapagliflozin is from 0.5 to 50 mg per day.

27. The composition according to any one of the preceding embodiments, wherein the dosage of said GLP-1 peptide or said GLP-1 derivative is from 0.1 to 100 mg per day, such as from 0.1 to 60 mg per day.

28. The composition according to any one of the preceding embodiments, wherein the dosage of said salt of NAC, such as SNAC, is 20-800 mg per day.

29. The composition according to any one of the preceding embodiments, wherein said composition is administered once daily.

30. The composition according any one of the preceding embodiments, wherein said GLP-1 derivative is semaglutide.

31. The composition according any one of the preceding embodiments, wherein said GLP-1 derivative is Compound A.

32. The composition according any one of the preceding embodiments, wherein said GLP-1 derivative is Compound B 33. The composition according any one of the preceding embodiments, wherein said GLP-1 derivative is Compound C.

34. The composition according any one of the preceding embodiments, wherein said GLP-1 derivative is Compound D.

35. The composition according any one of the preceding embodiments, wherein said GLP-1 derivative is Compound E.

36. The composition as defined in any one of the preceding embodiments for use in medicine.

37. The composition as defined in any one of the preceding embodiments for use in the prevention or treatment of diabetes or obesity.

38. A method for prevention or treatment of diabetes or obesity comprising administering a therapeutically effective amount of the composition as defined in any one of the preceding embodiments to a subject in need thereof.

EXAMPLES

List of Abbreviations

FD4: Fluorescein isothiocyanate-dextran 4 kD

Materials and Methods

Assay (I): Epithelial Cell Monolayer Culture and Test of Permeability

Cell Culturing

Caco-2 and NCl-N87 cells were obtained from the American Type Culture Collection (ATCC) (Manassas, Va.). Caco-2 cells were seeded in culturing flasks and passaged in Dulbecco's Modified Eagle' (DMEM) medium supplemented with 10% fetal bovine serum, 1% penicillin/streptomycin (100 U/ml and 100 µg/ml, respectively), 1% L-glutamine and 1% nonessential amino acids. Caco-2 cells were seeded onto tissue culture treated polycarbonate filters in 12-well Corning Transwell plates (1.13 $cm^2$, 0.4 µm pore size) at a density of $10^5$ cells/well.

NCl-N87 cells were cultured in Roswell Park Memorial Institute (RPMI) 1640 medium supplemented with 10% fetal bovine serum, 1% penicillin/streptomycin (100 U/ml and 100 µg/ml, respectively). N87 cells were seeded onto tissue culture treated polyester filters in 12-well Corning Transwell plates (1.13 $cm^2$, 0.4 µm pore size) at a density of $10^5$ cells/well.

Cell monolayers were grown in an atmosphere of 5% $CO_2$-95% $O_2$ at 37° C., replacing growth media every other day. The experiment was performed on day 14-16 after cell seeding.

Transepithelial Transport

The amount of test compound transported from the donor chamber (apical side) to the receiver chamber (basolateral side) was measured as described in [1] for Caco-2 monolayers and in [2] for NCl-N87 cell monolayers, in an atmosphere of 5% $CO_2$-95% $O_2$ at 37° C. on a shaking plate (30 rpm). Before the experiment, cell monolayers were equilibrated for 60 min with transport buffer on both sides of the epithelium. The transport buffer consisted of Hank's balanced saline solution containing 0.1% Ovalbumin (w/v), 0.005% Tween20 (w/w) and 10 mM HEPES, adjusted to pH 7.4. The transport of [$^3$H]mannitol (PerkinElmer), was measured to verify the integrity of the epithelium.

For Caco-2 cells the transport study was initiated by adding 400 µl solution of test compound(s) (transport buffer containing test compound(s) and 0.8 µCi/ml [$^3$H]mannitol; for example comprising one or more of 100 µM GLP-1 peptide, 540 µM FD4 (Sigma Aldrich item no. 46944), 0-80 mM SNAC, 0-2 mM empagliflozin and 0-3 mM dapagliflozin) to the donor chamber and 1 ml transport buffer to the receiver chamber, and receiver samples (200 µl) were taken every 15 min for 1 h. For NCl-N87 cells, following buffer equilibration cell monolayers were pre-incubated for 15 min with 400 μl solution of test compound (0-80 mM SNAC and/or 0-3 mM dapagliflozin), which were replaced by 400 μl solution of test compound (aqueous solution containing 0.8 μCi/ml [$^3$H]mannitol and either 100 μM GLP-1 peptide or 540 μM FD4) and receiver samples (200 μl) taken every 15 min for 1 h.

Translocation of a given compound across cell layers is expressed as the apparent permeability ($P_{app}$), given by:

$$P_{app} = \frac{dQ}{dt}\frac{1}{A \cdot C_0} \qquad \text{Eq. (1)}$$

where dQ/dt is the steady-state flux across the cell layer (pmol/s), A is the surface area (1.12 cm$^2$), and $C_0$ is the initial sample concentration.

Before and after the experiment the transepithelial electrical resistance (TEER) of the cell monolayers was monitored. After experiments, cells were washed twice with buffer and replenished with medium for 24 h TEER recovery to ensure that the cell monolayers were viable and the enhancer effects were transient. The TEER was measured with EVOM™ Epithelial Voltohmmeter connected to Chopsticks. For Caco-2 monolayers the starting TEER was typically around 1000 Ω·cm$^2$ and for N87 monolayers it was around 1600 Ω·cm$^2$.

Concentration of dapagliflozin and empagliflozin in stock solutions was verified by UPLC.

REFERENCES

[1] I. Hubatsch, E. G. E. Ragnarsson, P. Artursson, *Determination of drug permeability and prediction of drug absorption in Caco-2 monolayers*. Nat. Protoc. (2007) 2, 2111-9.

[2] M. Lemieux, F. Bouchard, P. Gosselin, J. Paquin, M. A. Mateescu, *The NCI-N87 cell line as a gastric epithelial barrier model for drug permeability assay*. Biochem Biophys Res Commun. (2011); 412(3):429-34.

General Methods

The concentration of semaglutide and Compound B was determined using a LOCI assay with an ELISA like principle. The concentration of dapagliflozin and empagliflozin in stock solutions was measured using UPLC. The concentration of FD4 was measured in a fluorescence plate reader. The concentration of [$^3$H]mannitol was measured in a scintillation counter.

Example 1: Dapagliflozin Enhances Oral Absorption of GLP-1

Permeability of semaglutide across a cellular layer was tested in the in vitro model system Assay (I) described herein; this assay is a model of absorption of compounds across the gastrointestinal tract, i.e. oral bioavailability. The permeability was assessed in both the widely used intestinal cell line Caco-2 and the more recently described gastric cell line N87, to encompass the various gastrointestinal conditions that may be relevant for semaglutide absorption. The results are shown in Tables 1-4.

TABLE 1

Semaglutide permeability across Caco-2 cell monolayers, alone or in the presence of SNAC or dapagliflozin; from 3 separate experiments.

| | Semaglutide permeability ($P_{app}$ (cm/s), 10$^{-8}$) | | |
|---|---|---|---|
| | Mean | SD | n |
| Semaglutide | 0.46 | 0.14 | 3 |
| Semaglutide + 80 mM SNAC | 17.5 | 6.7 | 12 |
| Semaglutide + 0.7 mM dapagliflozin | 0.55 | 0.05 | 4 |
| Semaglutide + 1.4 mM dapagliflozin | 0.74 | 0.14 | 4 |
| Semaglutide + 1.7 mM dapagliflozin | 1.05 | 0.17 | 4 |
| Semaglutide + 2 mM dapagliflozin | 3.63 | 0.45 | 4 |
| Semaglutide + 2.2 mM dapagliflozin | 7.06 | 2.62 | 4 |
| Semaglutide + 2.4 mM dapagliflozin | 22.3 | 19.1 | 8 |
| Semaglutide + 2.55 mM dapagliflozin | 39.1 | 23.5 | 7 |
| Semaglutide + 2.7 mM dapagliflozin | 58.8 | 22.2 | 7 |

SNAC and dapagliflozin elicited transient decreases in cell monolayer TEER (dose-dependently for dapagliflozin) down to ~25% of starting values, with recovery after 24 h in fresh medium. Non-recovering TEER was observed for >2.7 mM dapagliflozin and permeability values for these are not included.

Surprisingly, the results of this experiment (Table 1) showed that dapagliflozin acted as an enhancer of semaglutide permeability across the cellular monolayer for the tested compound, i.e. indicating that oral bioavailability of semaglutide would be increased in the presence of dapagliflozin.

TABLE 2

Compound B permeability across Caco-2 cell monolayers, alone or in the presence of SNAC or dapagliflozin; from 2 separate experiments.

| | Semaglutide permeability ($P_{app}$ (cm/s), 10$^{-8}$) | | |
|---|---|---|---|
| | Mean | SD | n |
| Compound B | 0.55 | 0.38 | 7 |
| Compound B + 80 mM SNAC | 1.03 | 0.41 | 6 |
| Compound B + 0.7 mM dapagliflozin | 0.24 | 0.21 | 2 |
| Compound B + 1.4 mM dapagliflozin | 0.64 | 0.28 | 5 |
| Compound B + 1.7 mM dapagliflozin | 0.29 | 0.08 | 5 |
| Compound B + 2 mM dapagliflozin | 0.44 | 0.24 | 5 |
| Compound B + 2.2 mM dapagliflozin | 1.00 | 0.48 | 6 |
| Compound B + 2.4 mM dapagliflozin | 4.33 | 3.79 | 6 |
| Compound B + 2.55 mM dapagliflozin | 12.2 | 5.29 | 5 |
| Compound B + 2.7 mM dapagliflozin | 25.2 | 13.87 | 7 |

SNAC and dapagliflozin elicited transient decreases in cell monolayer TEER (dose-dependently for dapagliflozin) down to ~25% of starting values, with recovery after 24 h in fresh medium. Non-recovering TEER was observed for >2.7 mM dapagliflozin and permeability values for these are not included.

Surprisingly, the results of this experiment (Table 2) showed that dapagliflozin acted as an enhancer of GLP-1 Compound B permeability across the cellular monolayer for the tested compound, i.e. indicating that oral bioavailability of Compound B would be increased in the presence of dapagliflozin.

The employed dapagliflozin solvate contains propylene glycol (1:1), which was tested alone to ascertain that the observed enhancer effects are caused by dapagliflozin. Up to 3.2 mM propylene glycol gave rise to no monolayer TEER decrease or permeability enhancement.

TABLE 3

Semaglutide permeability across NCI-N87 cell monolayers, alone or in the presence of SNAC or dapagliflozin.

| | Semaglutide permeability ($P_{app}$ (cm/s), $10^{-8}$) | | |
|---|---|---|---|
| | Mean | SD | n |
| Semaglutide | 2.23 | 0.11 | 4 |
| Semaglutide + 60 mM SNAC | 2.58 | 0.29 | 4 |
| Semaglutide + 80 mM SNAC | 11.35 | 1.75 | 4 |
| Semaglutide + 2 mM dapagliflozin | 2.83 | 0.74 | 4 |
| Semaglutide + 2.2 mM dapagliflozin | 9.45 | 2.81 | 4 |
| Semaglutide + 2.4 mM dapagliflozin | 20.3 | 6.46 | 4 |
| Semaglutide + 2.5 mM dapagliflozin | 30.5 | 7.63 | 4 |

SNAC and dapagliflozin elicited transient decreases in cell monolayer TEER down to ~20% of starting values, with recovery after 24 h in fresh medium. Non-recovering TEER was observed for mM dapagliflozin and permeability values for these are not included.

The data in Table 3 shows that dapagliflozin efficiently enhances semaglutide permeability through a gastric cell monolayer.

TABLE 4

FD4 permeability across NCI-N87 cell monolayers, alone or in the presence of SNAC or dapagliflozin; from 2 separate experiments.

| | FD4 permeability ($P_{app}$ (cm/s), $10^{-8}$) | | |
|---|---|---|---|
| | Mean | SD | n |
| FD4 | 1.4 | 0.6 | 8 |
| FD4 + 80 mM SNAC | 15.3 | 4.2 | 6 |
| FD4 + 1 mM dapagliflozin | 1.4 | 0.5 | 4 |
| FD4 + 2 mM dapagliflozin | 7.2 | 5.0 | 8 |
| FD4 + 2.2 mM dapagliflozin | 12.3 | 2.8 | 4 |
| FD4 + 2.4 mM dapagliflozin | 22.8 | 4.8 | 5 |
| FD4 + 2.5 mM dapagliflozin | 27.8 | 2.3 | 4 |

SNAC and dapagliflozin elicited transient decreases in cell monolayer TEER down to ~25% of starting values, with recovery after 24 h in fresh medium. Non-recovering TEER was observed for >2.6 mM dapagliflozin and permeability values for these are not included.

The results in Table 4 show that permeability of FD4 was increased dose-dependently by dapagliflozin.

Collectively, the above data surprisingly showed that dapagliflozin acted as an enhancer of semaglutide, compound B, and FD4 permeability across the cellular monolayer for the tested compound, i.e. indicating that oral bioavailability of semaglutide and Compound B would be increased in the presence of dapagliflozin.

Example 2: Dapagliflozin and SNAC Combination Provides Synergistic Oral Absorption Permeability of FD4 or semaglutide across a cellular layer was tested in the in vitro model system Assay (I) described herein; this assay is a model of absorption of compounds across the gastrointestinal tract, i.e. oral bioavailability. The results are shown in Tables 5-8.

TABLE 5

FD4 permeability across Caco-2 cell monolayers, alone or in the presence of SNAC, dapagliflozin or a combination thereof.

| | FD4 permeability ($P_{app}$ (cm/s), $10^{-8}$) | | |
|---|---|---|---|
| | Mean | SD | n |
| FD4 | 0.23 | 0.06 | 4 |
| FD4 + 40 mM SNAC | 0.17 | 0.03 | 3 |
| FD4 + 60 mM SNAC | 0.24 | 0.05 | 3 |
| FD4 + 80 mM SNAC | 0.82 | 0.19 | 4 |
| FD4 + 1 mM dapagliflozin | 0.16 | 0.01 | 3 |
| FD4 + 2 mM dapagliflozin | 0.42 | 0.09 | 4 |
| FD4 + 2.6 mM dapagliflozin | 6.01 | 0.78 | 4 |
| FD4 + 40 mM SNAC + 2 mM dapagliflozin | 1.54 | 0.23 | 4 |
| FD4 + 60 mM SNAC + 1 mM dapagliflozin | 1.89 | 0.91 | 4 |
| FD4 + 80 mM SNAC + 1 mM dapagliflozin | 19.33 | 3.22 | 4 |

SNAC, dapagliflozin and combinations thereof elicited transient decreases in cell monolayer TEER down to ~35% of starting values, with recovery after 24 h in fresh medium. Non-recovering TEER was observed for 3 mM dapagliflozin and 60 mM SNAC+2 mM dapagliflozin and permeability values for these are not included.

Surprisingly, the results of this experiment (Table 5) showed that the combination of dapagliflozin and SNAC provided a synergistic effect on the permeability across the cellular monolayer for FD4, i.e. indicating that oral bioavailability would be greater than the sum of the oral bioavailability with dapagliflozin alone or SNAC alone. The synergistic effect was confirmed for semaglutide in both cellular layers of Caco-2 (Table 6-7) and NCl-N87 (Table 8).

TABLE 6

Semaglutide permeability across Caco-2 cell monolayers, alone or in the presence of SNAC, dapagliflozin or a combination thereof.

| | Semaglutide permeability ($P_{app}$ (cm/s), $10^{-8}$) | | |
|---|---|---|---|
| | Mean | SD | n |
| Semaglutide | 0.9 | 0.4 | 4 |
| Semaglutide + 70 mM SNAC | 3.3 | 0.5 | 4 |
| Semaglutide + 70 mM SNAC + 1 mM dapagliflozin | 25.2 | 3.6 | 4 |
| Semaglutide + 70 mM SNAC + 1.5 mM dapagliflozin | 146.3 | 9.1 | 4 |
| Semaglutide + 80 mM SNAC | 9.2 | 1.5 | 4 |
| Semaglutide + 80 mM SNAC + 0.5 mM dapagliflozin | 25.7 | 5.0 | 4 |
| Semaglutide + 80 mM SNAC + 1 mM dapagliflozin | 91.5 | 11.5 | 4 |

Mixtures of SNAC and dapagliflozin elicited transient decreases in cell monolayer TEER down to ~35% of starting values, with recovery after 24 h in fresh medium. Non-recovering TEER was observed for 70 mM SNAC+2 mM dapagliflozin and 80 mM SNAC+1.5 mM dapagliflozin and permeability values for these are not included.

0.5-1.5 mM dapagliflozin was previously shown to have negligible effect alone on semaglutide permeability across Caco-2 cell monolayers.

TABLE 7

Compound B permeability across Caco-2 cell monolayers, alone or in the presence of SNAC, dapagliflozin or a combination thereof.

| | Semaglutide permeability ($P_{app}$ (cm/s), $10^{-8}$) | | |
|---|---|---|---|
| | Mean | SD | n |
| Compound B | 0.56 | 0.32 | 8 |
| Compound B + 80 mM SNAC | 0.92 | 0.49 | 6 |
| Compound B + 80 mM SNAC + 1 mM dapagliflozin | 4.01 | 1.03 | 7 |
| Compound B + 80 mM SNAC + 1.5 mM dapagliflozin | 39.57 | 28.79 | 7 |

Mixtures of SNAC and dapagliflozin elicited transient decreases in cell monolayer TEER down to ~35% of starting values, with recovery after 24 h in fresh medium. 0.5-2.0 mM dapagliflozin was previously shown to have negligible effect alone on Compound B permeability across Caco-2 cell monolayers.

TABLE 8

Semaglutide permeability across NCI-N87 cell monolayers, alone or in the presence of SNAC, dapagliflozin or a combination thereof.

| | Semaglutide permeability ($P_{app}$ (cm/s), $10^{-8}$) | | |
|---|---|---|---|
| | Mean | SD | n |
| Semaglutide | 0.4 | 0.02 | 3 |
| Semaglutide + 60 mM SNAC | 0.6 | 0.2 | 4 |
| Semaglutide + 60 mM SNAC + 1 mM dapagliflozin | 5.4 | 3.7 | 7 |
| Semaglutide + 70 mM SNAC | 2.6 | 0.3 | 4 |
| Semaglutide + 70 mM SNAC + 1 mM dapagliflozin | 7.5 | 1.7 | 4 |
| Semaglutide + 70 mM SNAC + 1.5 mM dapagliflozin | 53.7 | 8.5 | 3 |

Mixtures of SNAC and dapagliflozin elicited transient decreases in cell monolayer TEER down to ~15% of starting values, with recovery after 24 h in fresh medium. Non-recovering TEER was observed for 60 mM SNAC+2 mM dapagliflozin and permeability values for these are not included.

1-1.5 mM dapagliflozin was previously shown to have negligible effect alone on semaglutide permeability across NCI-N87 cell monolayers.

Surprisingly, the results of these experiments (Tables 5-8) showed that the combination of dapagliflozin and SNAC provided a synergistic effect on the permeability across the cellular monolayer of either Caco-2 or NCl-87 for semaglutide, Compound B and FD4, i.e. indicating that oral bioavailability of peptides, such as semaglutide and compound B, would be greater than the sum of its oral bioavailability with dapagliflozin alone or SNAC alone.

Example 3: Empagliflozin and SNAC Combination Provides Synergistic Oral Absorption Permeability of semaglutide or FD4 across a cellular layer was tested in the in vitro model system Assay (I) described herein; this assay is a model of absorption of compounds across the gastrointestinal tract, i.e. oral bioavailability. The results are shown in Tables 9-10.

TABLE 9

Semaglutide permeability across Caco-2 cell monolayers, alone or in the presence of SNAC or a combination of SNAC and empagliflozin.

| | Semaglutide permeability ($P_{app}$ (cm/s), $10^{-8}$) | | |
|---|---|---|---|
| | Mean | SD | n |
| Semaglutide | 0.20 | 0.03 | 3 |
| Semaglutide + 80 mM SNAC | 0.55 | 0.25 | 7 |
| Semaglutide + 1.2 mM empagliflozin | 0.64 | N.A. | 1 |
| Semaglutide + 1.5 mM empagliflozin | 0.10 | N.A. | 1 |
| Semaglutide + 80 mM SNAC + 0.6 mM empagliflozin | 0.63 | 0.18 | 8 |
| Semaglutide + 80 mM SNAC + 0.9 mM empagliflozin | 0.77 | 0.26 | 8 |
| Semaglutide + 80 mM SNAC + 1.2 mM empagliflozin | 1.02 | 0.44 | 7 |
| Semaglutide + 80 mM SNAC + 1.5 mM empagliflozin | 2.81 | 2.88 | 6 |

N.A.: Not available

TABLE 10

FD4 permeability across Caco-2 cell monolayers, alone or in the presence of SNAC, empagliflozin or a combination thereof; from 2 separate experiments.

| | FD4 permeability ($P_{app}$ (cm/s), $10^{-8}$) | | |
|---|---|---|---|
| | Mean | SD | n |
| FD4 | 5.09 | 3.99 | 6 |
| FD4 + 80 mM SNAC | 5.96 | 4.41 | 5 |
| FD4 + 90 mM SNAC | 8.69 | 4.41 | 4 |
| FD4 + 1.2 mM empagliflozin | 0.71 | 0.70 | 8 |
| FD4 + 1.5 mM empagliflozin | 0.58 | 0.25 | 3 |
| FD4 + 80 mM SNAC + 0.6 mM empagliflozin | 7.90 | 6.39 | 8 |
| FD4 + 80 mM SNAC + 0.9 mM empagliflozin | 6.28 | 1.96 | 4 |
| FD4 + 80 mM SNAC + 1.2 mM empagliflozin | 31.36 | 18.34 | 7 |
| FD4 + 80 mM SNAC + 1.5 mM empagliflozin | 38.44 | 4.34 | 4 |

SNAC, empagliflozin and combinations thereof elicited transient decreases in cell monolayer TEER down to ~35% of starting values, with recovery after 24 h in fresh medium.

Surprisingly, the results of these experiments (Tables 9-10) showed that the combination of empagliflozin and SNAC provided a synergistic effect on the permeability across the cellular monolayer of Caco-2 for semaglutide and FD4, i.e. indicating that oral bioavailability of peptides, such as semaglutide would be greater than the sum of its oral bioavailability with dapagliflozin alone or SNAC alone.

Formulations with semaglutide and dapagliflozin versus semaglutide were repeated in vivo with comparable results.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

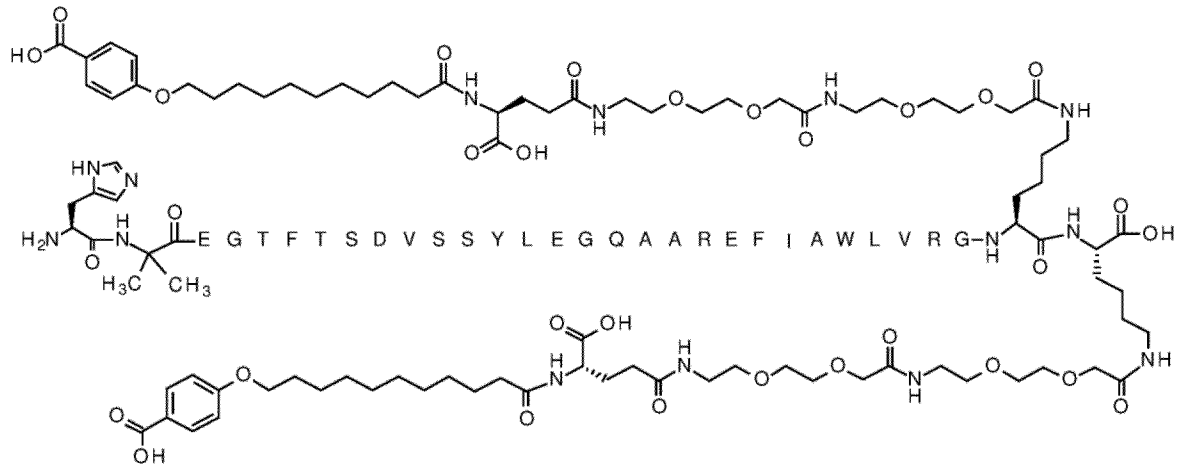

The invention claimed is:

1. A solid pharmaceutical composition for oral administration comprising a GLP-1 derivative and dapagliflozin, wherein the GLP-1 derivative is selected from the group consisting of:
   (a) $N^{\varepsilon26}$\{2-[2-(2-\{2-[2-(2-\{(S)-4-Carboxy-4-[10-(4-carboxyphenoxy)decanoylamino]butyrylamino\}ethoxy)ethoxy]acetylamino\}ethoxy)ethoxy]acetyl\}, $N^{\varepsilon37}$-\{2-[2-(2-\{2-[2-(2-\{(S)-4-carboxy-4-[10-(4-carboxyphenoxy)decanoylamino]butyrylamino\}ethoxy)ethoxy]acetylamino\}ethoxy)ethoxy] acetyl\}-[Aib$^8$,Arg$^{34}$, Lys$^{37}$] GLP-1(7-37)-peptide (Compound A)
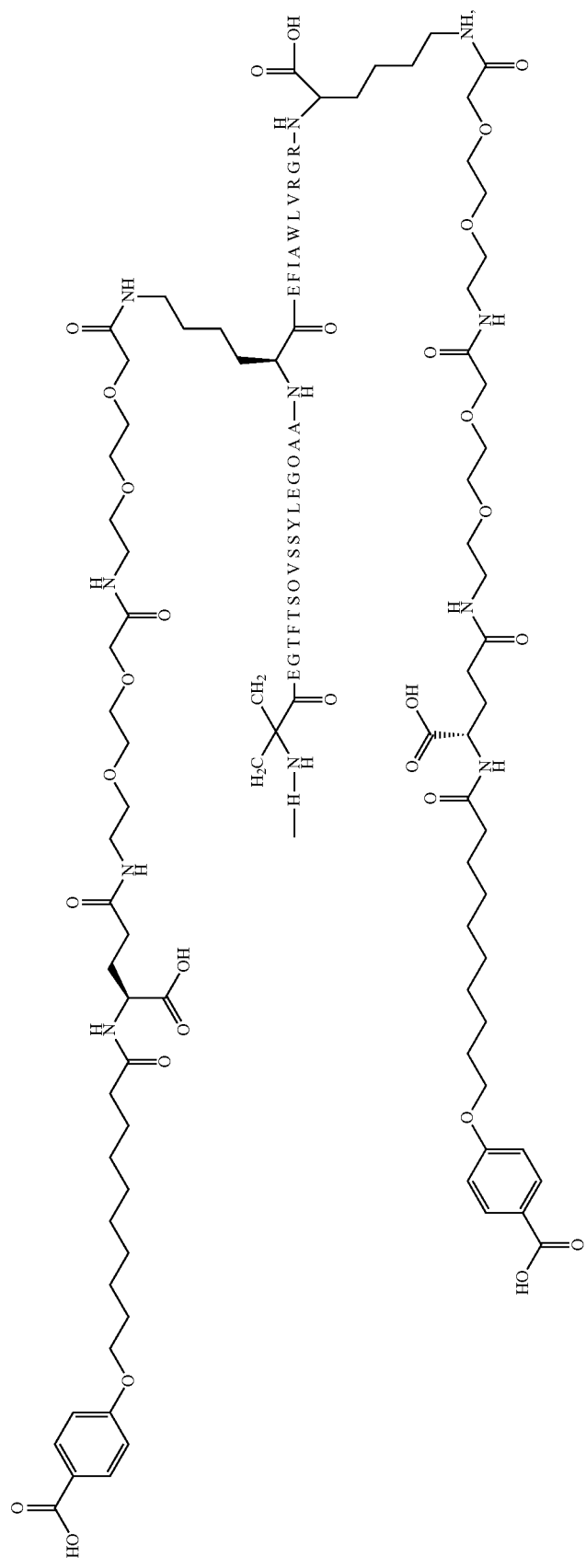

(b) $N^{\varepsilon37}$-[2-[2-[2-[[2-[2-[2-[[(4S)-4-carboxy-4-[10-(4-carboxyphenoxy)decanoylamino]butanoyl]amino]ethoxy] ethoxy]acetyl] amino]ethoxy]ethoxy]acetyl], $N^{\varepsilon36}$-[2-[2-[2-[[2-[2-[2-[[(4S)-4-carboxy-4-[10-(4-carboxy-phenoxy) decanoylamino] butanoyl] amino]eth-oxy]ethoxy]acetyl] amino]ethoxy] ethoxy]acetyl]-[Aib8,Glu22,Arg26,Lys27,Glu30,Arg34,Lys36]-GLP-1-(7-37)-peptidyl-Glu-Gly (Compound B)
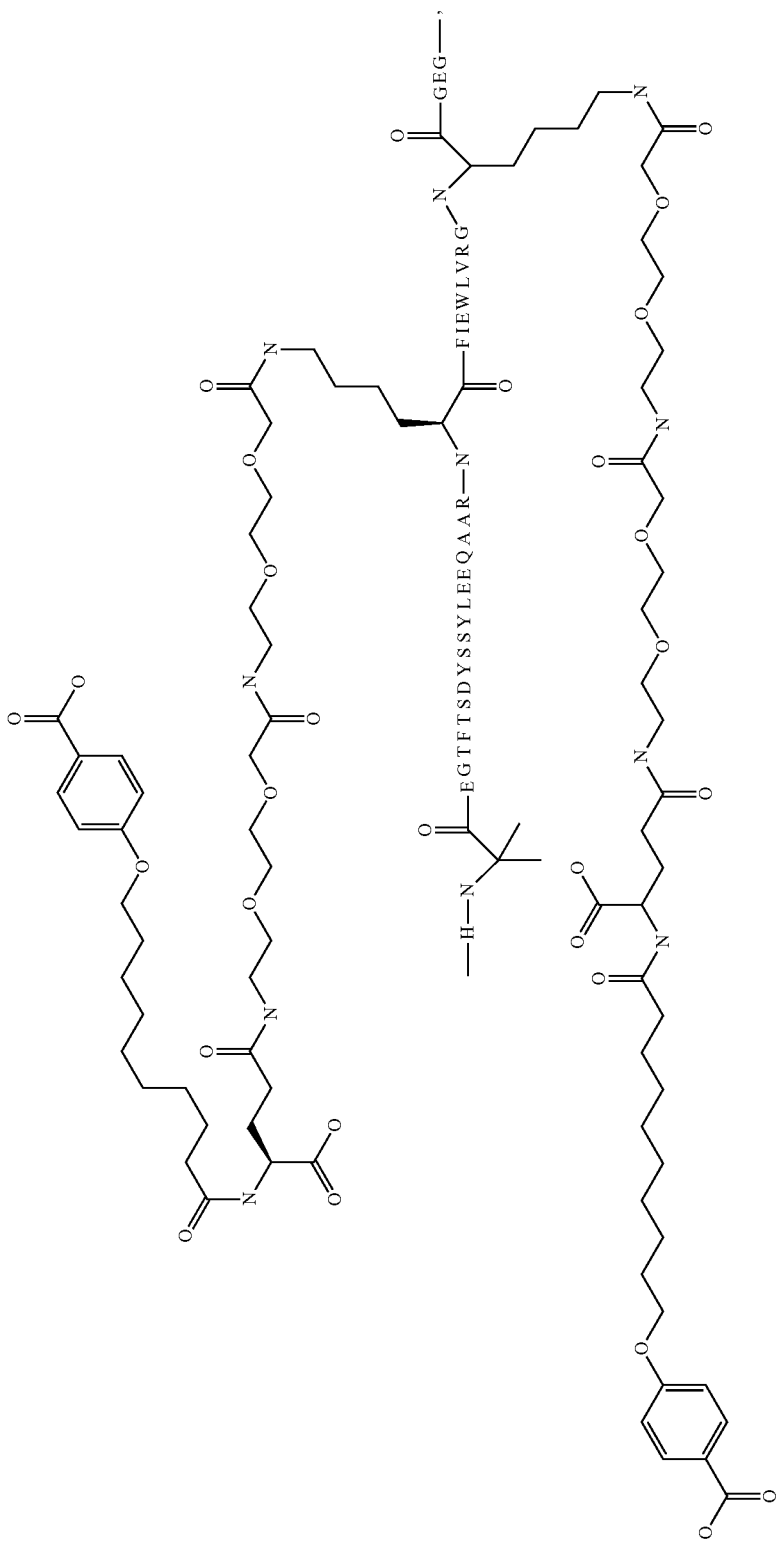

(c) N {Epsilon-36}-[2-[2-[2-[[2-[2-[2-[[(4S)-4-carboxy-4-[11-(4-carboxyphenoxy)undecanoylamino]butanoyl]amino] ethoxy] ethoxy] acetyl]amino]ethoxy] ethoxy] acetyl],N {Epsilon-371-[2-[2-[2-[[2-[2-[2-[[(4S)-4-carboxy-4-[11-(4-carboxyphenoxy)undecanoylamino] butanoyl]amino]ethoxy] ethoxy]acetyl]amino]ethoxy] ethoxy]acetyl]-[Aib8,Glu22,Arg26,Arg34,Lys36, Lys37]-GLP-1-(7-37)-peptide (Compound C)
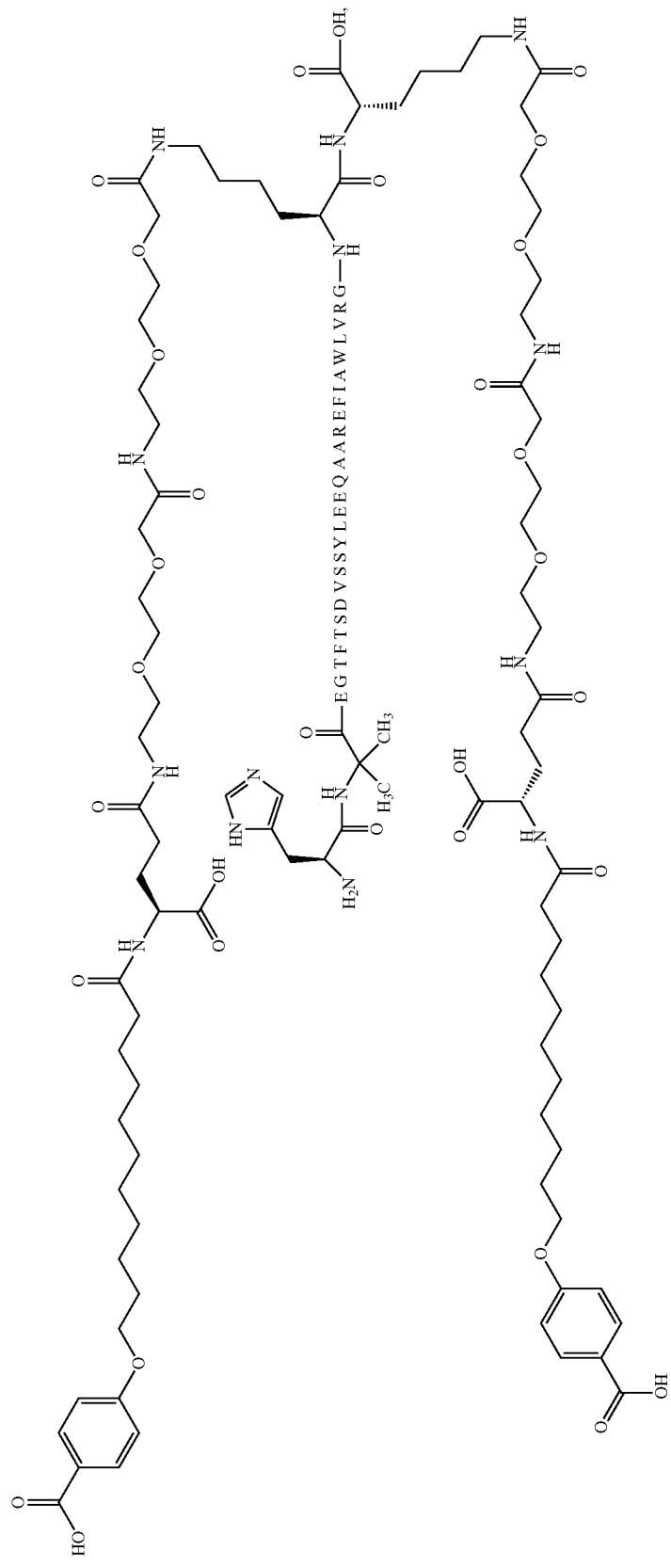

(d) N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy] acetyl]amino]ethoxy]ethoxy]acetyl],N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide

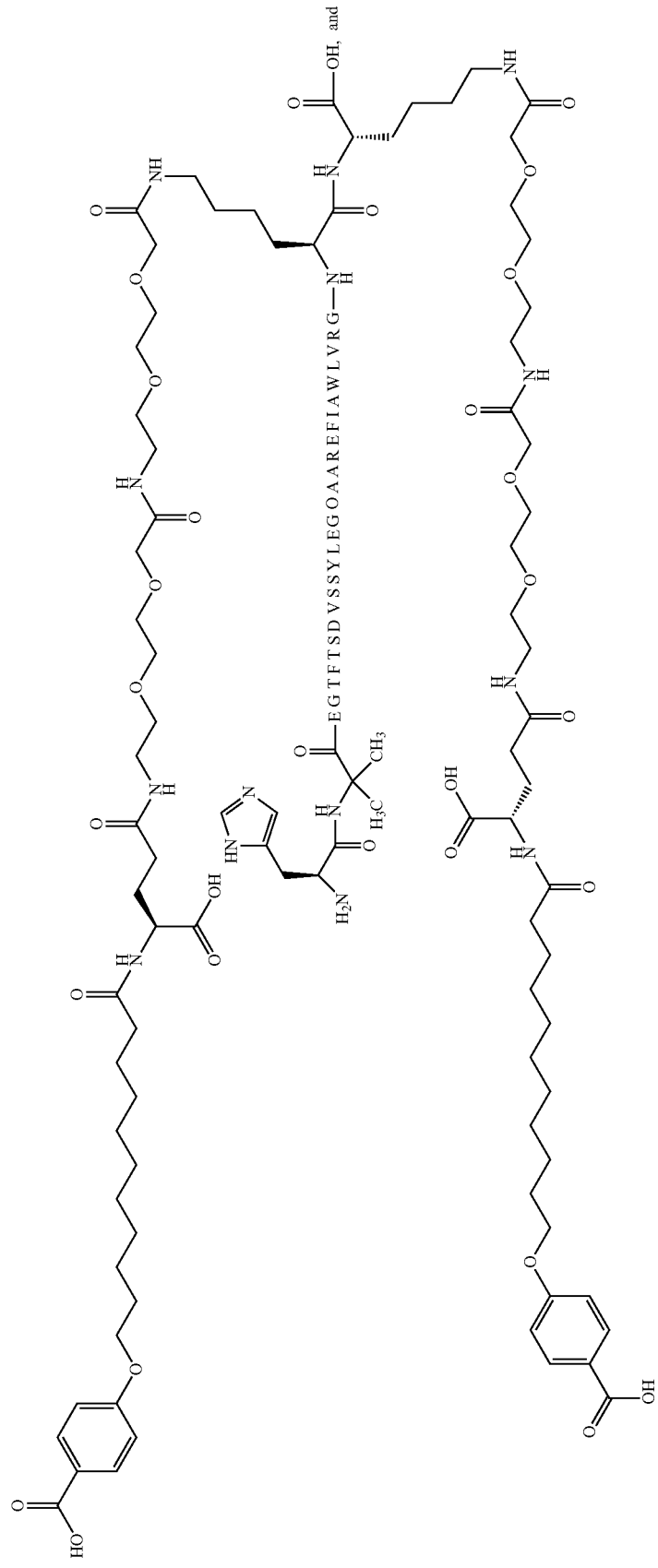

(e) N{Epsilon-36}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl],N{Epsilon-37}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Compound E)
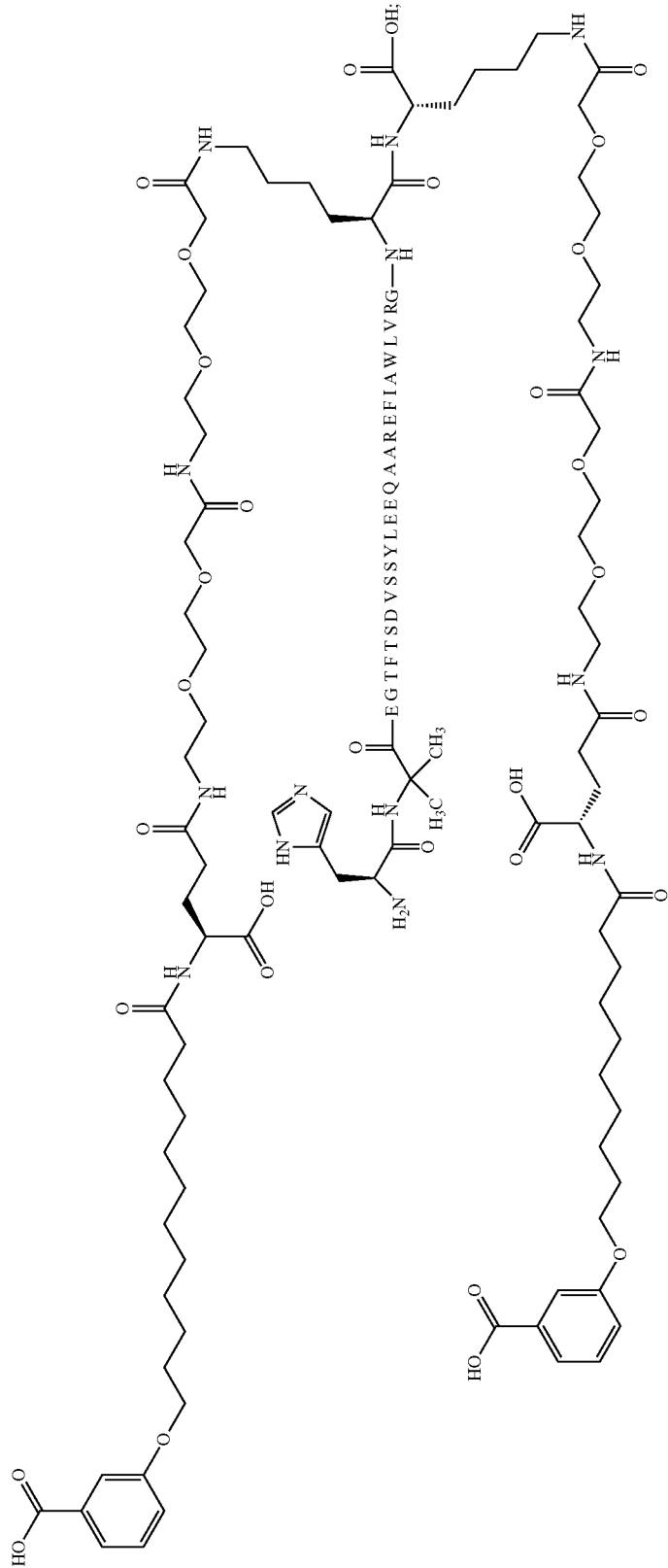

wherein the oral bioavailability of the GLP-1 derivative is increased in the presence of dapagliflozin.

2. The solid pharmaceutical composition according to claim 1, wherein the GLP-1 derivative is Compound B.

3. The pharmaceutical composition according to claim 1, wherein the composition further comprises an absorption enhancer.

4. The composition according to claim 3, wherein the absorption enhancer is N-(8-(2-hydroxybenzoyl)amino) caprylate (NAC).

5. The pharmaceutical composition according to claim 4, wherein the absorption enhancer is a salt of NAC.

6. The pharmaceutical composition according to claim 5, wherein the salt of NAC is monosodium N-[8-(2-hydroxybenxoyl) amino] caprylate (SNAC) or polymorphs thereof.

7. The pharmaceutical composition according to claim 1, wherein one or both of the GLP-1 derivative and the dapagliflozin is in the form of a pharmaceutically acceptable salt, ester, or solvate.

8. The pharmaceutical composition according to claim 1, wherein the dosage of the dapagliflozin is 0.5-50 mg per day and the dosage of the GLP-1 derivative is 0.1-100 mg per day.

9. The pharmaceutical composition according to claim 1, wherein the composition comprises one or more additional pharmaceutically acceptable excipients.

10. The pharmaceutical composition according to claim 1, wherein the dosage of the composition administered is in the range of 200-1000 mg.

11. The pharmaceutical composition according to claim 1, wherein the composition is administered once daily.

12. The pharmaceutical composition according to claim 1, wherein the composition comprises 5-300 mg dapagliflozin and 20-800 mg of a salt of NAC.

13. The pharmaceutical composition according to claim 12, wherein the salt of NAC is SNAC or polymorphs thereof.

14. The pharmaceutical composition according to claim 1, wherein the composition is in a form selected from the group consisting of a tablet, a capsule, and a sachet.

15. A method of treating type 2 diabetes in a subject in need of such method comprising administering to the subject a therapeutically effective amount of the pharmaceutical composition according to claim 1 and one or more pharmaceutically acceptable excipients.

* * * * *

UNITED STATES PATENT AND TRADEMARK OFFICE
CERTIFICATE OF CORRECTION

PATENT NO. : 11,167,014 B2
APPLICATION NO. : 16/620363
DATED : November 9, 2021
INVENTOR(S) : Andreas Vegge et al.

Page 1 of 2

It is certified that error appears in the above-identified patent and that said Letters Patent is hereby corrected as shown below:

In the Claims

At Claim number 1, Column number 55, please replace with the following formula:

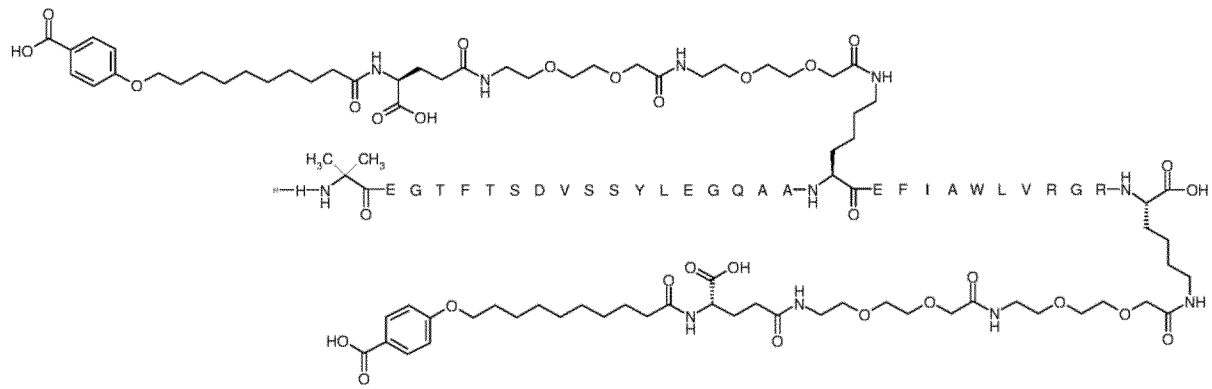

At Claim number 1, Column number 61, Line number 4 please replace {Epsilon-371}-[2-[2-[2-[[2-[2-[2-[[(4S)-4- with the following:
{Epsilon-37}-[2-[2-[2-[[2-[2-[2-[[(4S)-4-

Signed and Sealed this
Twenty-eighth Day of June, 2022

*Katherine Kelly Vidal*

Katherine Kelly Vidal
*Director of the United States Patent and Trademark Office*

CERTIFICATE OF CORRECTION (continued)
U.S. Pat. No. 11,167,014 B2

At Claim number 1, Column number 67, please replace with the following formula: